US011795235B2

(12) United States Patent
Pastan et al.

(10) Patent No.: US 11,795,235 B2
(45) Date of Patent: Oct. 24, 2023

(54) IMMUNOTOXINS WITH ALBUMIN BINDING DOMAIN

(71) Applicant: The United States of America, as represented by the Secretary, Department of Health and Human Services, Bethesda, MD (US)

(72) Inventors: Ira H. Pastan, Chevy Chase, MD (US); Junxia Wei, Rockville, MD (US); Masanori Onda, Germantown, MD (US); Tapan Bera, Frederick, MD (US); Mitchell Ho, Urbana, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 72 days.

(21) Appl. No.: 16/648,369

(22) PCT Filed: Sep. 18, 2018

(86) PCT No.: PCT/US2018/051418
§ 371 (c)(1),
(2) Date: Mar. 18, 2020

(87) PCT Pub. No.: WO2019/055955
PCT Pub. Date: Mar. 21, 2019

(65) Prior Publication Data

US 2020/0223937 A1 Jul. 16, 2020

Related U.S. Application Data

(60) Provisional application No. 62/559,926, filed on Sep. 18, 2017.

(51) Int. Cl.
*C07K 14/21* (2006.01)
*C07K 16/28* (2006.01)
*C07K 16/30* (2006.01)

(52) U.S. Cl.
CPC .............. *C07K 16/30* (2013.01); *C07K 14/21* (2013.01); *C07K 16/2803* (2013.01); *C07K 16/2866* (2013.01); *C07K 16/2878* (2013.01); *C07K 2317/31* (2013.01); *C07K 2317/569* (2013.01); *C07K 2317/624* (2013.01); *C07K 2317/73* (2013.01); *C07K 2317/94* (2013.01); *C07K 2319/33* (2013.01); *C07K 2319/50* (2013.01); *C07K 2319/55* (2013.01); *C07K 2319/70* (2013.01)

(58) Field of Classification Search
CPC .... C07K 16/30; C07K 14/21; C07K 16/2803; C07K 16/2878; C07K 2317/569; C07K 2317/624; C07K 2319/33; C07K 2319/50
See application file for complete search history.

(56) References Cited

U.S. PATENT DOCUMENTS

| | | | |
|---|---|---|---|
| 9,388,222 B2 | 7/2016 | Pastan et al. | |
| 2012/0009123 A1 | 1/2012 | Trieu | |
| 2014/0154248 A1 * | 6/2014 | Pastan | A61P 35/00 424/134.1 |
| 2015/0044208 A1 | 2/2015 | Castanheira Aires da Silva et al. | |
| 2016/0354472 A1 | 12/2016 | Merchant | |

FOREIGN PATENT DOCUMENTS

WO WO-2005097202 A2 * 10/2005 ............ A61K 47/64

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Alewine et al., "Advances in Anticancer Immunotoxin Therapy," *The Oncologist*, 20: 176-185 (2015).
Bera et al., "A Bivalent Disulfide-stablized Fv with Improved Antigen Binding to erbB2," *Journal of Molecular Biology*, 281: 475-483 (1998).

(Continued)

*Primary Examiner* — Meera Natarajan
*Assistant Examiner* — Cheom-Gil Cheong
(74) *Attorney, Agent, or Firm* — Leydig, Voit & Mayer, Ltd.

(57) ABSTRACT

Disclosed is a molecule comprising: (a) a first domain, which comprises a targeting moiety; (b) a second domain, which comprises an albumin binding domain (ABD), (c) a third domain, which comprises a furin cleavage sequence ("FCS"), which FCS is cleavable by furin; and (d) a fourth domain, which comprises an optionally substituted Domain III from *Pseudomonas* exotoxin A ("PE"). Related nucleic acids, recombinant expression vectors, host cells, populations of cells, pharmaceutical compositions, methods of producing the molecule, methods of treating or preventing cancer in a mammal, and methods of inhibiting the growth of a target cell are also disclosed.

18 Claims, 36 Drawing Sheets

Specification includes a Sequence Listing.

(56) References Cited

OTHER PUBLICATIONS

Figure 1C:
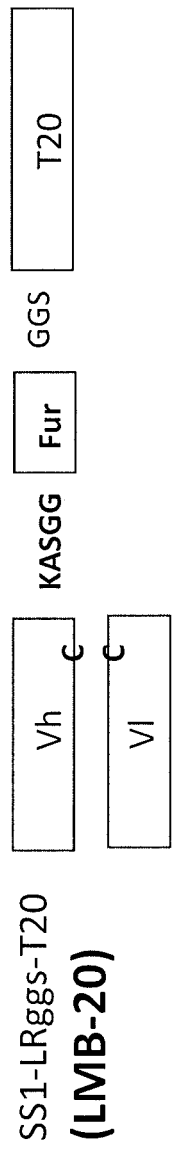
Figure 1D:
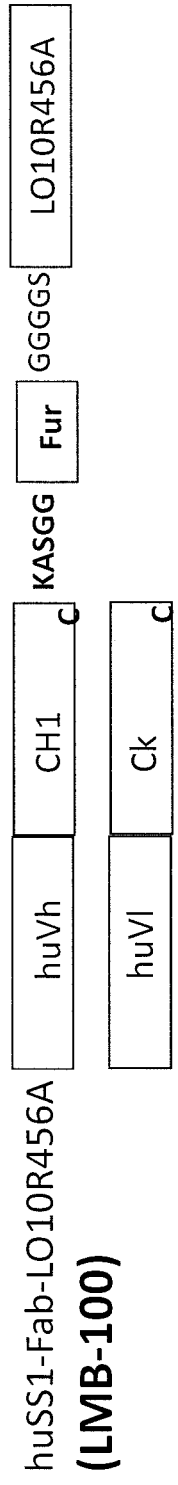

Bera et al., "Bivalent Disulfie-stabilized Fragment Variable Immunotoxin Directed against Mesotheliomas and Ovarian Cancer," *Molecular Cancer Therapeutics*, 1: 79-84 (2001).

Coppieters et al., "Formatted Anti-Tumor Necrosis Factor α VHH Proteins Derived From Camelids Show Superior Potency and Targeting to Inflamed Joints in a Murine Model of Collagen-Induced Arthritis," *Arthritis & Rheumatism*, 54(6): 1856-1866(2006).

European Patent Office, International Search Report in International Patent Application No. PCT/US2018/051418, dated Dec. 21, 2018.

European Patent Office, Written Opinion in International Patent Application No. PCT/US2018/051418, dated Dec. 21, 2018.

Guo et al., "Fusion of an albumin-binding domain extends the half-life of immunotoxins," *International Journal of Pharmaceutics*, 511: 538-549 (2016).

Jonsson et al., "Engineering of a femtomolar affinity binding protein to human serum albumin," *Protein Engineering, Design & Selection*, 21(8): 515-527 (2008).

Kontermann, "Strategies for extended serum half-life of protein therapeutics," *Current Opinion in Biotechnology*, 22: 868-876 (2011).

Li et al., "Clinical targeting recombinant immunotoxins for cancer therapy," *OncoTargets and Therapy*, 10: 3645-3665 (2017).

Liu et al., "Target-specific cytotoxic effects on HER2-expressing cells by the tripartite fusion toxin $Z_{HER2:2891}$-ABD-PE38X8, including a targeting affibody molecule and half-life extension domain," *International Journal of Oncology*, 47: 601-609 (2015).

Mazor et al., "Rational design of low immunogenic anti CD25 recombinant immunotoxin for T cell malignancies by elimination of T cell epitopes in PE38," *Cellular Immunology*, 313: 59-66 (2017).

Mazor et al., "Recombinant Immunotoxin with T-cell Epitope Mutations That Greatly Reduce Immunogenicity for Treatment of Mesothelin-Expressing Tumors," *Molecular Cancer Therapeutics*, 14(12): 2789-2796 (2015).

Onda et al., "Mutants of Immunotoxin Anti-Tac(dsFv)-PE38 with Variable Number of Lysine Residues as Candidates for Site-Specific Chemical Modification. 1. Properties of Mutant Molecules," *Bioconjugate Chem.*, 14: 480-487 (2003).

Onda et al., "Prolonged Half-life of Recombinant Immunotoxins in Mice by Adding an Albumin Binding Domain," *The FASEB Journal*, 31(1 supplement): 1-3 (2017).

Shancer et al., "Preclinical development of anti-BCMA immunotoxins targeting multiple myeloma," *Antibody Therapeutics*, 1(1): 19-25 (2018).

Wei et al., "Recombinant immunotoxins with albumin-binding domains have long half-lives and high antitumor activity," *PNAS*, 115(15): E3501-E3508 (2018).

Mazor et al., "Identification and elimination of an immunodominant T-cell epitope in recombinant immunotoxins based on Pseudomonas exotoxin A," *Proc. Natl. Acad. Sci. USA*, 109(51): E3597-E3603 (Dec. 3, 2012).

Mazor et al., "Recombinant immunotoxin for cancer treatment with low immunogenicity by identification and silencing of human T-cell epitopes," *Proc. Natl. Acad. Sci. USA*, 111(23): 8571-8576 (Jun. 10, 2014).

\* cited by examiner

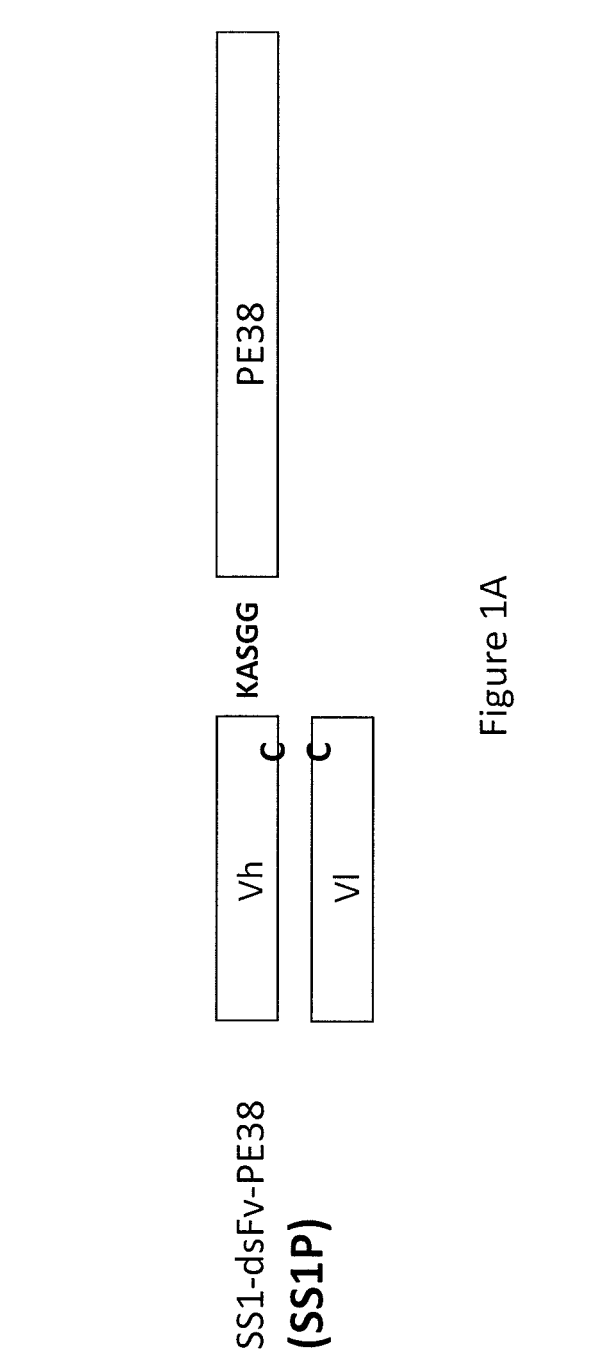

SS1-ABD-LRggs
(LMB-164)

SS1-ALB1-LRggs
(LMB-170)

SS1-MSA21-LRggs
(LMB-172)

SS1-ABD-PE38
(LMB-209)

BM306-bdsFv-LRggs

HA22-bdsFv-LRggs

BM24-bdsFv-LRggs e23-bdsFv-PE38

SS1 dsFv-T20
(LMB-20)

SS1-ABD-dsFv-T20
(LMB-182)

SS1-ALB1-dsFv-LRGGS
(LMB-170)

SS1-MSA21-dsFv-LRGGS
(LMB-172)

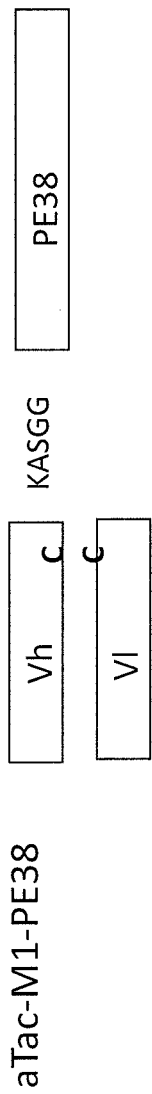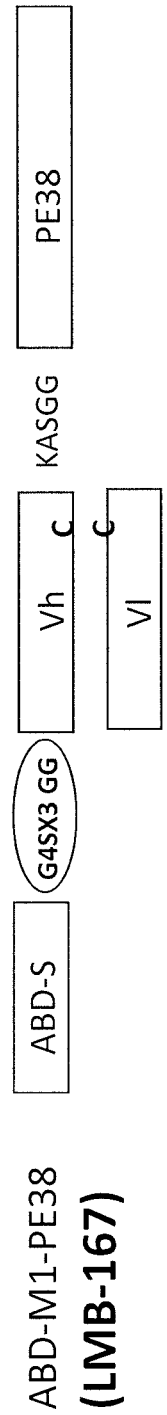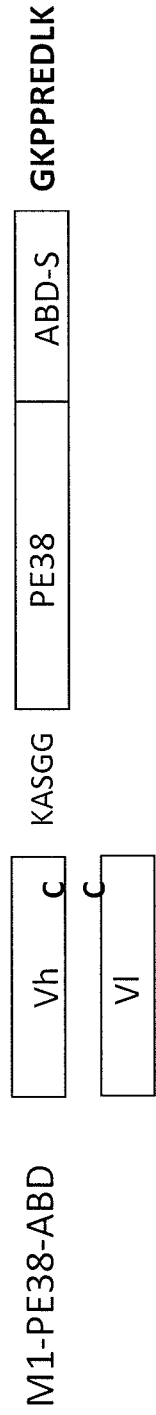
Figure 12A
Figure 12B
Figure 12C
aTac-M1-PE38
ABD-M1-PE38
(LMB-167)
M1-PE38-ABD BM306-dsFv-LRggs
(LMB-75)

BM306-ABD-LRggs
(LMB-162)

HA22-dsFv-LRggs
(LMB-13)

HA22-ABD-LRggs
(LMB-196)

BM306-ABD-lin-Vh
(LMB-235)

BM306-ABD-Lin-Vl
(LMB-237)

SEQUENCE LISTING

<160> NUMBER OF SEQ ID NOS: 38

<210> SEQ ID NO 1
<211> LENGTH: 613
<212> TYPE: PRT
<213> ORGANISM: Pseudomonas aeruginosa

<400> SEQUENCE: 1

-continued

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
```

```
                420                 425                 430
Gly Tyr Val Phe Val Gly Tyr His Gly Thr Phe Leu Glu Ala Ala Gln
            435                 440                 445

Ser Ile Val Phe Gly Gly Val Arg Ala Arg Ser Gln Asp Leu Asp Ala
        450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Leu Pro Gly Phe Tyr
            500                 505                 510

Arg Thr Ser Leu Thr Leu Ala Ala Pro Glu Ala Gly Glu Val Glu
        515                 520                 525

Arg Leu Ile Gly His Pro Leu Pro Leu Arg Leu Asp Ala Ile Thr Gly
            530                 535                 540

Pro Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 2
<211> LENGTH: 54
<212> TYPE: PRT
<213> ORGANISM: Group G streptococcus

<400> SEQUENCE: 2

Pro Gly Ser Ser Leu Gln Val Asp Leu Ala Glu Ala Lys Val Leu Ala
1               5                   10                  15

Asn Arg Glu Leu Asp Lys Tyr Gly Val Ser Asp Tyr Tyr Lys Asn Leu
            20                  25                  30

Ile Asn Asn Ala Lys Thr Val Glu Gly Val Lys Ala Leu Ile Asp Glu
        35                  40                  45

Ile Leu Ala Ala Leu Pro
    50

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Arg Glu Asp Leu
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 4

Lys Asp Glu Leu
1

<210> SEQ ID NO 5
<211> LENGTH: 11
<212> TYPE: PRT
<213> ORGANISM: Pseudomonas aeruginosa

<400> SEQUENCE: 5

Arg His Arg Gln Pro Arg Gly Trp Glu Gln Leu
1               5                   10

<210> SEQ ID NO 6
<211> LENGTH: 5
<212> TYPE: PRT
<213> ORGANISM: Pseudomonas aeruginosa

<400> SEQUENCE: 6

Arg Glu Asp Leu Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Lys Ala Ser Gly Gly
1               5

<210> SEQ ID NO 8
<211> LENGTH: 3
<212> TYPE: PRT
<213> ORGANISM: Artificial Sequence
<220> FEATURE:
<223> OTHER INFORMATION: Synthetic

<400> SEQUENCE: 8

Gly Gly Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: wherein X is any naturally occurring amino acid
<220> FEATURE:
<221> NAME/KEY: MISC_FEATURE
<222> LOCATION: (3)..(3)
<223> OTHER INFORMATION: wherein X is any naturally occurring amino acid

<400> SEQUENCE: 9

Arg Xaa Xaa Arg
1

<210> SEQ ID NO 10
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 10

Arg Lys Lys Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Arg Arg Arg Arg
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Arg Lys Ala Arg
1

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Ser Arg Val Ala Arg Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Thr Ser Ser Arg Lys Arg Arg Phe Trp
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ala Ser Arg Arg Lys Ala Arg Ser Trp
1               5

<210> SEQ ID NO 16
<211> LENGTH: 8
<212> TYPE: PRT
<213> ORGANISM: Artificial Sequence
<220> FEATURE:
```

```
<223> OTHER INFORMATION: Synthetic

<400> SEQUENCE: 16

Arg Arg Val Lys Lys Arg Phe Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Arg Asn Val Val Arg Arg Asp Trp
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Thr Arg Ala Val Arg Arg Arg Ser Trp
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Arg Gln Pro Arg
1

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Arg His Arg Gln Pro Arg Gly Trp
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Arg His Arg Gln Pro Arg Gly Trp Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 22

His Arg Gln Pro Arg Gly Trp Glu Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Arg Gln Pro Arg Gly Trp Glu
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Arg His Arg Ser Lys Arg Gly Trp Glu Gln Leu
1               5                   10

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Arg Ser Lys Arg
1

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Arg His Arg Ser Lys Arg Gly Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

His Arg Ser Lys Arg Gly Trp Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 28

Arg Ser Lys Arg Gly Trp Glu Gln Leu
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

His Arg Ser Lys Arg Gly Trp Glu Gln Leu
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Arg His Arg Ser Lys Arg
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is any naturally occurring amino acid
<220> FEATURE:
<221> NAME/KEY: MISC_FEATURE
<222> LOCATION: (3)..(3)
<223> OTHER INFORMATION: X is arginine or lysine

<400> SEQUENCE: 31

Arg Xaa Xaa Arg
1

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Gly Gly Gly Gly Ser
1               5

<210> SEQ ID NO 33
<211> LENGTH: 15
<212> TYPE: PRT
<213> ORGANISM: Artificial Sequence
<220> FEATURE:
<223> OTHER INFORMATION: Synthetic

<400> SEQUENCE: 33

Gly Gly Gly Gly Ser Gly Gly Gly Gly Ser Gly Gly Gly Gly Ser
1               5                   10                  15
```

```
<210> SEQ ID NO 34
<211> LENGTH: 3
<212> TYPE: PRT
<213> ORGANISM: Artificial Sequence
<220> FEATURE:
<223> OTHER INFORMATION: Synthetic

<400> SEQUENCE: 34

Ser Gly Gly
1

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Gly Gly Gly Gly Ser Gly Gly Gly Ser Gly Gly Gly Gly Ser Gly
1               5                   10                  15

Gly

<210> SEQ ID NO 36
<211> LENGTH: 9
<212> TYPE: PRT
<213> ORGANISM: Pseudomonas aeruginosa

<400> SEQUENCE: 36

Gly Lys Pro Pro Arg Glu Asp Leu Lys
1               5

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Gly Ser Gly Ser Gly Ser Gly Ser Gly Ser Gly Ser Gly Ser Gly Ser
1               5                   10                  15

Gly

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Gly Ser Gly Ser Gly Ser Gly Ser Gly
1               5
```

IMMUNOTOXINS WITH ALBUMIN BINDING DOMAIN

CROSS-REFERENCE TO RELATED APPLICATION

This patent application is the U.S. National phase of International Patent Application No. PCT/US2018/051418, filed Sep. 18, 2018, which claims the benefit of U.S. Provisional Patent Application No. 62/559,926, filed Sep. 18, 2017, each of which is incorporated by reference in its entirety herein.

STATEMENT REGARDING FEDERALLY SPONSORED RESEARCH OR DEVELOPMENT

This invention was made with Government support under project number Z01 BC008753, awarded by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 12,678 bytes Byte ASCII (Text) file named "747687 ST25.txt," dated Mar. 4, 2020.

BACKGROUND OF THE INVENTION

*Pseudomonas* exotoxin A (PE) is a bacterial toxin with cytotoxic activity that may be effective for destroying or inhibiting the growth of undesirable cells, e.g., cancer cells. Accordingly, PE may be useful for treating or preventing diseases such as, e.g., cancer. While PE can produce positive clinical responses in some cancer patients, there is a need for improved PE.

BRIEF SUMMARY OF THE INVENTION

An embodiment of the invention provides a molecule comprising: (a) a first domain, which comprises a targeting moiety, wherein the targeting moiety is not an affibody; (b) a second domain, which comprises an albumin binding domain (ABD), (c) a third domain, which comprises a furin cleavage sequence ("FCS") which FCS is cleavable by furin; and (d) a fourth domain, which comprises an optionally substituted Domain III from *Pseudomonas* exotoxin A ("PE"); wherein the molecule optionally has (i) a substitution of one or more amino acid residues within one or more T-cell epitopes, (ii) a substitution of one or more amino acid residues within one or more B cell epitopes, (iii) a deletion of one or more contiguous amino acid residues of residues 1-273 and 285-394 as defined by SEQ ID NO:1; or (iv) a combination of any of (i)-(iii).

Another embodiment of the invention provides a molecule comprising a sequence of Formula (I):

$$\text{TM-R}^1{}_k\text{-ABD-R}^2{}_m\text{-FCS-R}^3{}_p\text{-R}^4{}_q\text{-PE functional domain III} \quad \text{(Formula I)}$$

wherein:

TM is a targeting moiety;

$R^1$ is 1 to 20 amino acid residues;

k, m, p, and q are, independently, 0 or 1;

ABD is an albumin binding domain;

$R^2$ is 1 to 20 amino acid residues;

FCS is a furin cleavage sequence of amino acid residues, which sequence is cleavable by furin and has an amino end and a carboxyl end;

$R^3$ is 1 to 20 amino acid residues;

$R^4$ is 1 or more contiguous residues of residues 365-394 of SEQ ID NO: 1; and

PE functional domain III is residues 395-613 of *Pseudomonas* exotoxin A (PE) SEQ ID NO: 1, wherein the molecule has a deletion of amino acid residues 253-273 and 285-364 as defined by SEQ ID NO: 1; and wherein the molecule optionally has (i) a substitution of one or more amino acid residues within one or more T-cell epitopes, (ii) a substitution of one or more amino acid residues within one or more B cell epitopes, (iii) a deletion of one or more contiguous amino acid residues of residues 1-252 as defined by SEQ ID NO:1; or (iv) a combination of any of (i)-(iii).

Additional embodiments of the invention provide related nucleic acids, recombinant expression vectors, host cells, populations of cells, pharmaceutical compositions, and methods of producing the inventive molecule.

Still another embodiment of the invention provides a method of treating or preventing cancer in a mammal comprising administering to the mammal the inventive molecule, nucleic acid, recombinant expression vector, host cell, population of cells, or pharmaceutical composition, in an amount effective to treat or prevent cancer in the mammal.

Another embodiment of the invention provides a method of inhibiting the growth of a target cell comprising contacting the cell with the inventive molecule, nucleic acid, recombinant expression vector, host cell, population of cells, or pharmaceutical composition, in an amount effective to inhibit growth of the target cell.

BRIEF DESCRIPTION OF THE SEVERAL VIEWS OF THE DRAWING(S)

FIG. 1A is a schematic of recombinant immunotoxin (RIT) construct SS1-dsFv-PE38, "SS1P." SS1P is an immunotoxin containing SS1 construct wherein the heavy chain variable region (Vh) and variable chain light fragment (Vl) (together, the variable domain or Fv) are fused to each other through disulfide bonds formed via cysteine residues (C). The Fv is fused to a 38 kDa portion of *Pseudomonas* exotoxin A (PE38) via a KASGG linker (SEQ ID NO: 7).

FIG. 1B is a schematic of RIT construct SS1-LRggs, ("LMB-12"). LMB-12 is an immunotoxin containing an SS1 construct wherein the Fv is fused to an 11 amino acid furin cleavage sequence (Fur), via a KASGG linker (SEQ ID NO: 7). The Vh and Vl of the Fv are fused to each other through disulfide bonds formed via cysteine residues (C). The 11 amino acid Fur is fused to a 24 kDa portion of PE (PE24) via linker GGS (SEQ ID NO: 8).

FIG. 1C is a schematic of RIT construct SS1-LRggs-T20, ("LMB-20"). LMB-20 is an immunotoxin containing an SS1 construct wherein the Vh and Vl of the Fv are fused to each other through disulfide bonds formed via cysteine residues (C). The Fv is fused to Fur, via a KASGG linker (SEQ ID NO: 7). The 11 amino acid Fur is fused to T20 (a highly potent RIT targeted at mesothelin expressing cancers which has 8 T cell epitopes removed) via a GGS linker (SEQ ID NO: 8).

FIG. 1D is a schematic of humanized RIT construct SS1-Fab-L010R456A, ("LMB-100"). LMB-100 is an immunotoxin containing an SS1 construct wherein the Fab fragment is composed of a humanized Vh and a human CH1 constant region, and a humanized Vl and a human Ck constant region. The CH1 and Ck of the Fv are fused to each other through disulfide bonds formed via cysteine residues (C). The Fab fragment is fused to the 11 amino acid Fur via a 5 amino acid KASGG linker (SEQ ID NO: 7). Fur is fused to LO10R456A via a GGGGS linker (SEQ ID NO: 32).

Figure 2A:
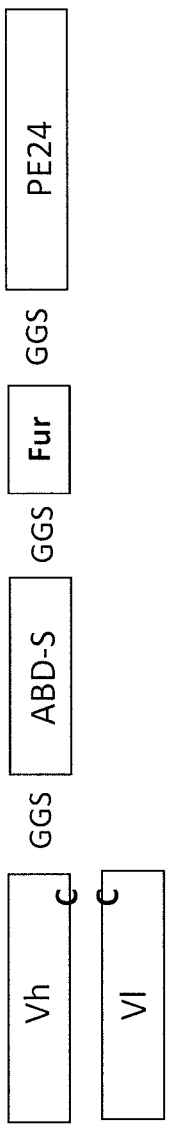

FIG. 2A is a schematic of RIT construct SS1-ABD-LRggs, ("LMB-164"). LMB-164 is an immunotoxin containing an SS1-albumin binding construct based on parent SS1-LRggs (FIG. 1B) wherein the Vh and Vl of the Fv are fused to each other through disulfide bonds formed via cysteine residues (C). LMB-164 has inserted a 54 amino acid albumin binding domain sequence ("ABD-S") (SEQ ID NO: 2) which is fused to the Fv and to the 11 amino acid Fur via 3 amino acid GGS linkers (SEQ ID NO: 8). Fur is fused to PE24 via a 3 amino acid GGS linker (SEQ ID NO: 8).

Figure 2B:
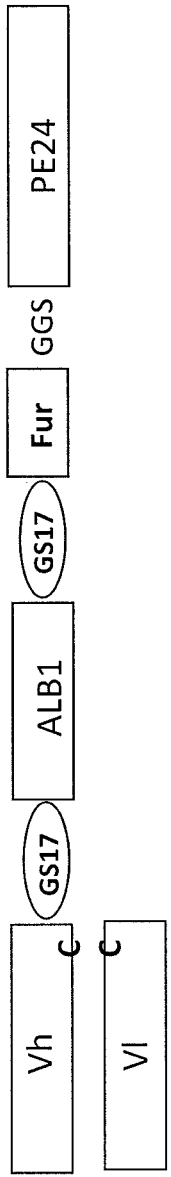

FIG. 2B is a schematic of RIT construct SS1-ALB1-LRggs, ("LMB-170"). LMB-170 is an immunotoxin containing an SS1-albumin binding construct based on parent RIT SS1-LRggs (FIG. 1B) wherein the Vh and Vl of the Fv are fused to each other through disulfide bonds formed via cysteine residues (C). LMB-170 has inserted a 115 amino acid single domain antibody from Llama ("ALB1") which is fused to the Fv and to 11 amino acid Fur via peptide linkers GS17, which are 17 amino acids in length (SEQ ID NO: 37). Fur is fused to PE24 via a 3 amino acid GGS linker (SEQ ID NO: 8).

Figure 2C:
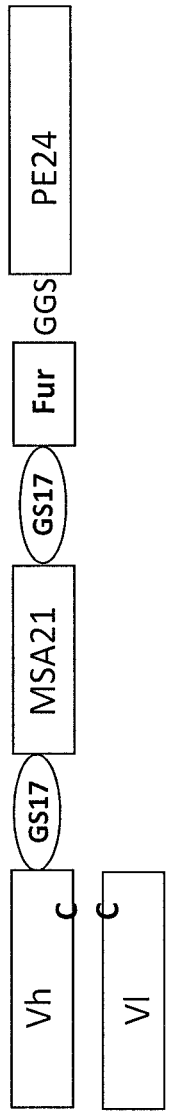

FIG. 2C is a schematic of RIT construct SS1-MSA21-LRggs, ("LMB-172"). LMB-172 is an SS1-albumin binding construct based on parent RIT SS1-LRggs (FIG. 1B). The Vh and Vl of the Fv are fused to each other through disulfide bonds formed via cysteine residues (C). LMB-172 has inserted a 115 amino acid single domain antibody from Llama ("MSA21") which is fused to the Fv and to Fur via peptide linkers GS17, which are 17 amino acids in length (SEQ ID NO: 37). Fur is fused to PE24 via a 3 amino acid GGS linker (SEQ ID NO: 8).

Figure 2D:
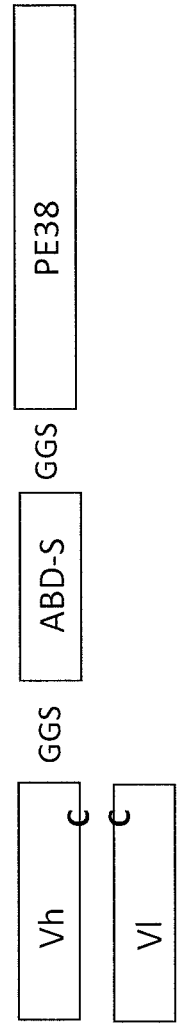

FIG. 2D is a schematic of RIT construct SS1-ABD-PE38, ("LMB-209"). LMB-209 is an SS1-albumin binding construct based on parent SS1-dsFv-PE38 (FIG. 1A). The Vh and Vl of the Fv are fused to each other through disulfide bonds formed via cysteine residues (C). LMB-209 has inserted a 54 amino acid albumin binding domain sequence "(ABD-S") (SEQ ID NO: 2) which is attached to the Fv and to PE38 via 3 amino acid GGS linkers (SEQ ID NO: 8).

Figure 3A:
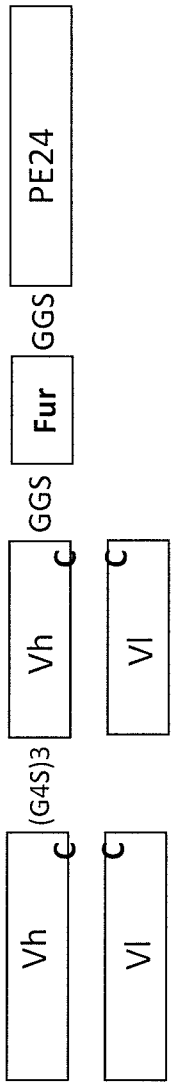

FIG. 3A is a schematic of RIT construct BM306-bdsFv-LRggs, which includes the Fv of an anti-BCMA antibody attached to a second Fv via a GGGGSGGGGSGGGGS ("(G4S)₃") linker (SEQ ID NO: 33), which is, in turn, fused to Fur via a GGS linker (SEQ ID NO: 8). The Vh and Vl of the first Fv are fused to each other through disulfide bonds formed via cysteine residues (C). The Vh and Vl of the second Fv are fused to each other through disulfide bonds formed via cysteine residues (C). Fur is fused to a 24 kDa portion of PE (PE24) via linker GGS (SEQ ID NO: 8).

Figure 3B:
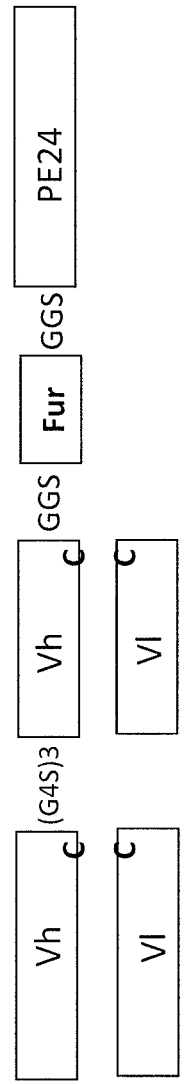

FIG. 3B is a schematic of RIT construct HA22-bdsFv-LRggs, which includes the Fv of an anti CD22 antibody attached to a second Fv via a (G4S)₃ linker (SEQ ID NO: 33), which is, in turn, fused to Fur via a GGS linker (SEQ ID NO: 8). The Vh and Vl of the first Fv are fused to each other through disulfide bonds formed via cysteine residues (C). The Vh and Vl of the second Fv are fused to each other through disulfide bonds formed via cysteine residues (C). Fur is fused to a 24 kDa portion of PE (PE24) via linker GGS (SEQ ID NO: 8).

Figure 3C:
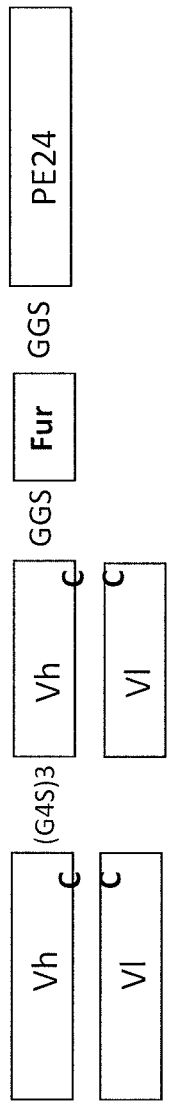

FIG. 3C is a schematic of RIT construct BM24-bdsFv-LRggs, which includes the Fv of an anti-BCMA antibody attached to the Fv via a (G4S)₃ linker (SEQ ID NO: 33), which is, in turn, fused to Fur via a GGS linker (SEQ ID NO: 8). The Vh and Vl of the first Fv are fused to each other through disulfide bonds formed via cysteine residues (C). The Vh and Vl of the second Fv are fused to each other through disulfide bonds formed via cysteine residues (C). Fur is fused to a 24 kDa portion of PE (PE24) via linker GGS (SEQ ID NO: 8).

Figure 3D:
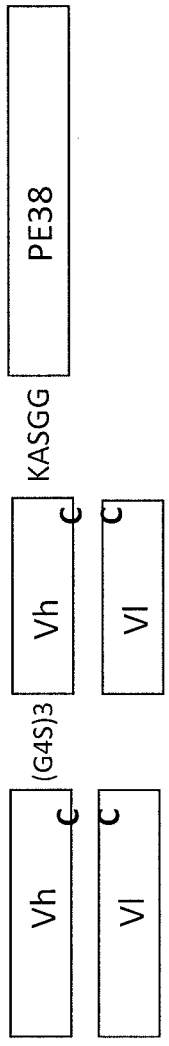

FIG. 3D is a schematic of RIT construct e23-bdsFv-PE38, which includes the Fv of monoclonal antibody "(Mab") e23 (an antibody directed against the erbB2 antigen which is present on many human carcinomas) attached to a second Fv via a (G4S)₃ linker (SEQ ID NO: 33). The Vh and Vl of the first Fv are fused to each other through disulfide bonds formed via cysteine residues (C). The Vh and Vl of the second Fv are fused to each other through disulfide bonds formed via cysteine residues (C), and fused to a 38 kDa portion of PE (PE38) via linker KASGG (SEQ ID NO: 7).

Figure 3E:
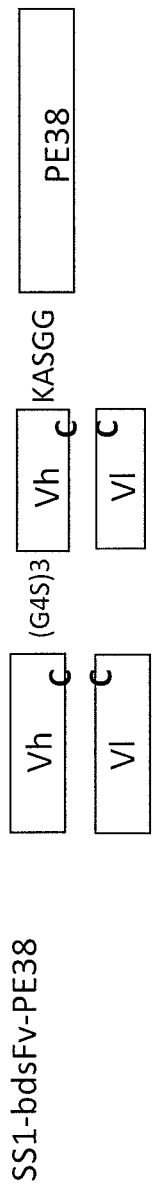

FIG. 3E is a schematic of RIT construct SS1-bdsFv-PE38, which includes the Fv from an anti-mesothelin antibody attached to a second Fv via a (G4S)₃ linker (SEQ ID NO: 33). The Vh and Vl of the first Fv are fused to each other through disulfide bonds formed via cysteine residues (C). The Vh and Vl of the second Fv are fused to each other through disulfide bonds formed via cysteine residues (C), and fused to a 38 kDa portion of PE (PE38) via linker KASGG (SEQ ID NO: 7).

Figure 3F:

FIG. 3F is a schematic of RIT construct SS1-scFv-HB21 scFv-PE24, which includes the Vh of SS1 fused to the Vl of SS1 via a (G4S)₃ linker (SEQ ID NO: 33). The SS1-Vl is in turn fused to the Vh of HB21 (from anti-CD71 antibody HB21 via a (G4S)₃ linker (SEQ ID NO: 33). HB21-Vh is in turn fused to the Vl of HB21 via a (G4S)₃ linker (SEQ ID NO: 33), which is, in turn, fused to Fur via an SGG linker (SEQ ID NO. 34). Fur is fused to a 24 kDa portion of PE (PE24) via linker GGS (SEQ ID NO: 8).

Figure 3G:

FIG. 3G is a schematic of RIT construct HB21-scFv-SS1 scFv-PE24, which includes the Vh of HB21 fused to the Vl of HB21 via a (G4S)₃ linker (SEQ ID NO: 33). HB21-Vl is, in turn, fused to the Vh of SS1 via a (G4S)₃ linker (SEQ ID NO: 33), which is, in turn, fused to the Vl of SS1 via a (G4S)₃ linker (SEQ ID NO: 33). SS1-Vl is fused to Fur via an SGG linker (SEQ ID NO. 34). Fur is fused to a 24 kDa portion of PE (PE24) via linker GGS (SEQ ID NO: 8).

Figure 4A:
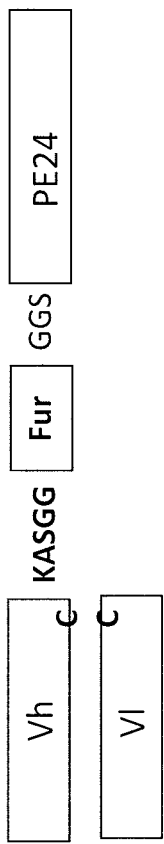

FIG. 4A is a schematic of RIT construct SS1-LRggs, ("LMB-12"). LMB-12 is an immunotoxin containing SS1 construct wherein the Fv is fused to an 11 amino acid furin cleavage sequence (Fur), via a 5 amino acid KASGG linker (SEQ ID NO: 7). The Vh and Vl of the Fv are fused to each other through disulfide bonds formed via cysteine residues (C). Fur is fused to a 24 kDa portion of PE (PE24) via 3 amino acid linker GGS (SEQ ID NO: 8).

Figure 4B:
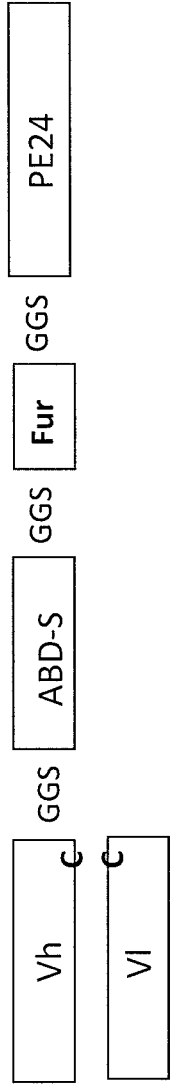

FIG. 4B is a schematic of RIT construct SS1-ABD-dsFv-LRGGS, ("LMB-164"). LMB-164 is an immunotoxin containing an SS1-albumin binding construct based on parent SS1-LRggs (FIG. 1B) wherein the Vh and Vl of the Fv are fused to each other through disulfide bonds formed via cysteine residues (C). LMB-164 has inserted a 54 amino acid albumin binding domain sequence named ABD-S (SEQ ID NO: 2) which is attached to the Fv and to Fur via 3 amino acid GGS linkers (SEQ ID NO: 8).

Figure 4C:
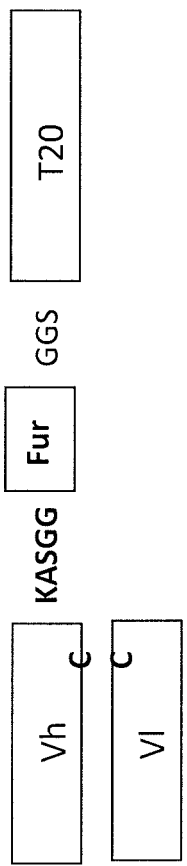

FIG. 4C is a schematic of RIT construct SS1 dsFv-T20, ("LMB-20"). LMB-20 is an immunotoxin containing an SS1 construct wherein the Vh and Vl of the Fv are fused to each other through disulfide bonds formed via cysteine residues (C). The Fv is fused to the 11 amino acid Fur, via a 5 amino acid KASGG linker (SEQ ID NO: 7). Fur is fused to T20 (a highly potent RIT targeted at mesothelin expressing cancers which has 8 T cell epitopes removed) via a 3 amino acid GGS linker (SEQ ID NO: 8).

Figure 4D:
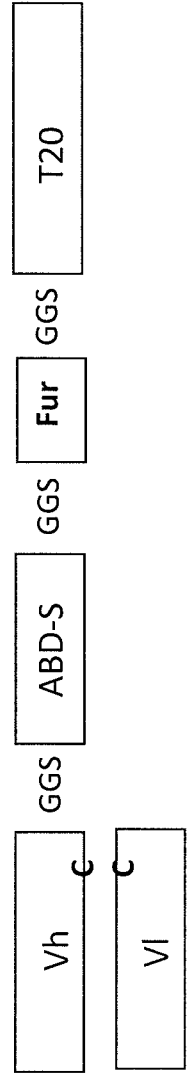

FIG. 4D is a schematic of RIT construct SS1-ABD-dsFV-T20, ("LMB-182"). LMB-182 is an immunotoxin containing an SS1 construct wherein the Vh and Vl of the Fv are fused to each other through disulfide bonds formed via cysteine residues (C). LMB-182 has inserted a 54 amino acid albumin binding domain sequence ("ABD-S") (SEQ ID NO: 2), which is fused to the Fv via a GGS linker (SEQ ID NO: 8). ABD-S is fused to Fur via a GGS linker (SEQ ID NO: 8). Fur is fused to T20 via a GGS linker (SEQ ID NO: 8).

Figure 4E:
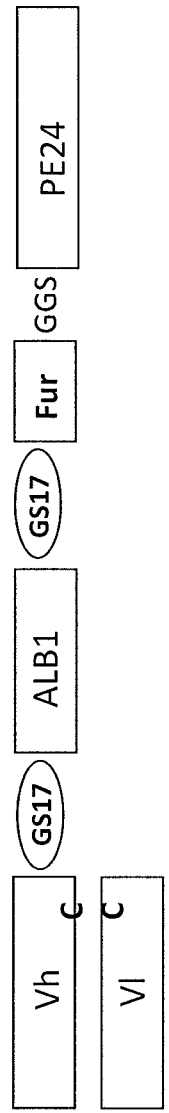

FIG. 4E is a schematic of RIT construct SS1-ALB1-dsFv-LRGGS, ("LMB-170"). LMB-170 is an immunotoxin containing an SS1-albumin binding construct based on parent RIT SS1-LRggs (FIG. 1B) wherein the Vh and Vl of the Fv are fused to each other through disulfide bonds formed via cysteine residues (C). LMB-170 has inserted a 115 amino acid single domain antibody from Llama named ALB1 which is attached to the Fv and to Fur via 17 amino acid peptide linkers GS17 (SEQ ID NO: 35).

Figure 4F:
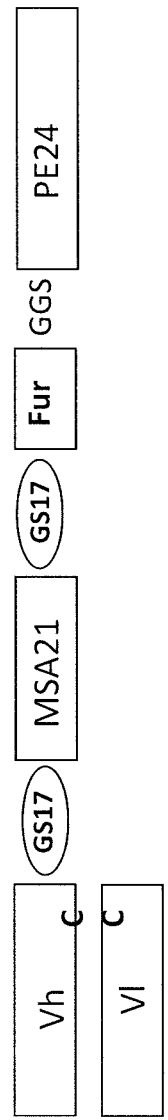

FIG. 4F is a schematic of RIT construct SS1-MSA-21-dsFv-LRGGS, ("LMB-172"). LMB-172 is an SS1-albumin binding construct from parent RIT SS1-LRggs (FIG. 1B). The Vh and Vl of the Fv are fused to each other through disulfide bonds formed via cysteine residues (C). LMB-172 has inserted a 115 amino acid single domain antibody from Llama named MSA21 which is attached to the Fv and to Fur via 17 amino acid peptide linkers GS17 (SEQ ID NO: 35).

Figure 5:
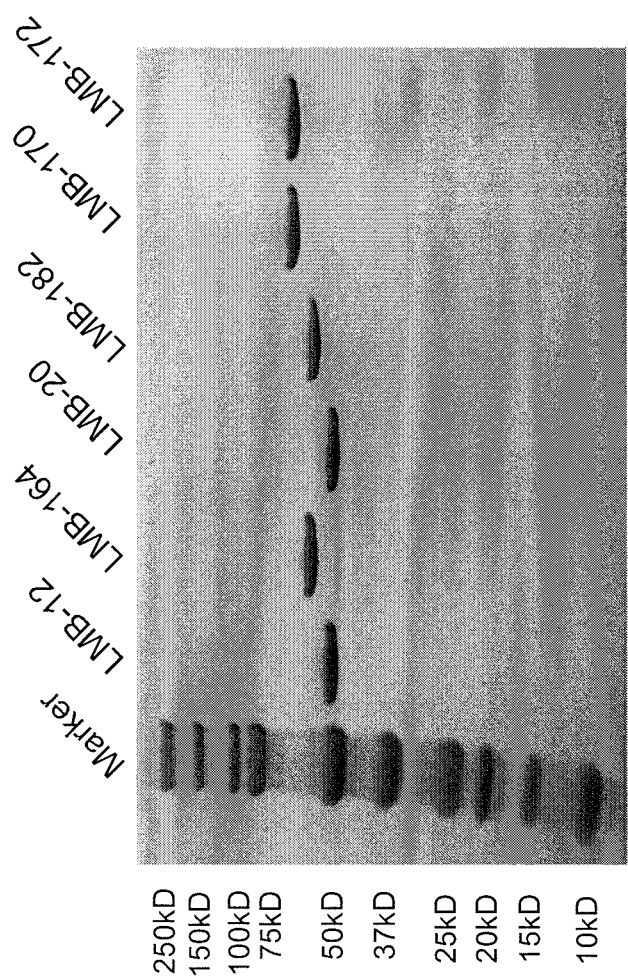
Figure 6A:
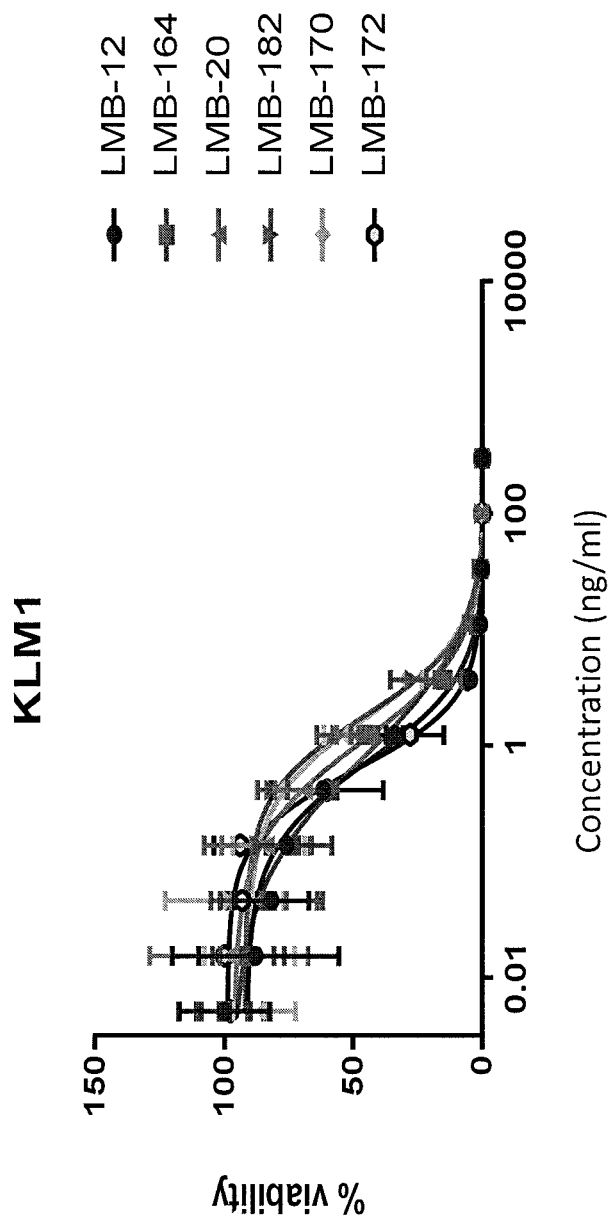
Figure 6B:
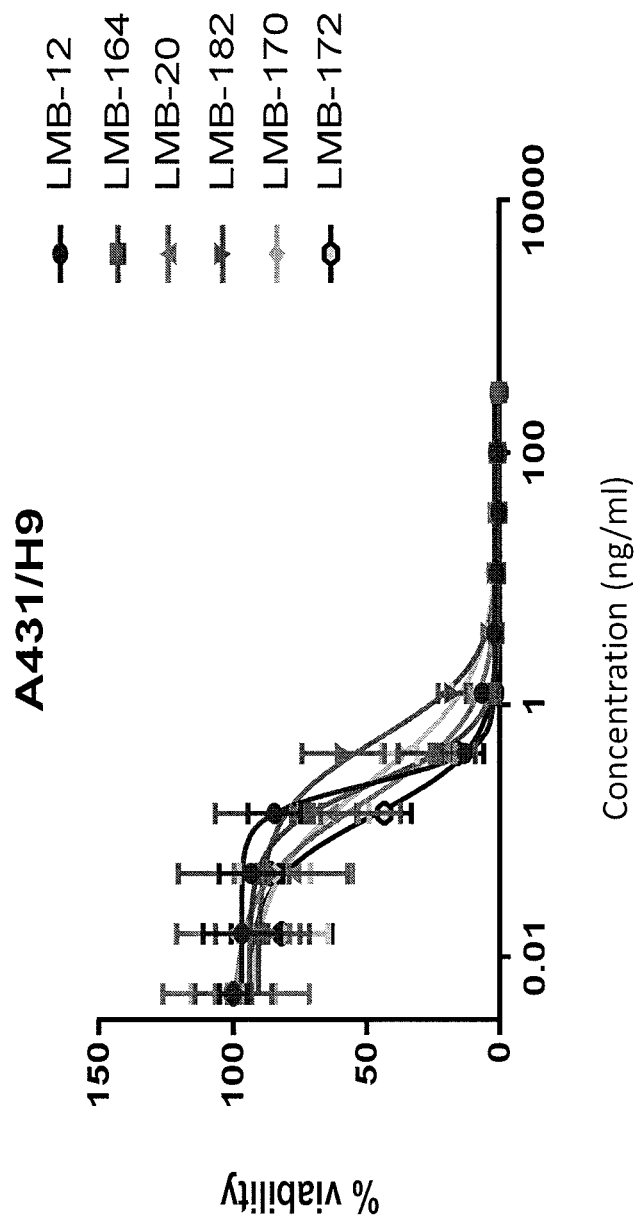
Figure 6C:
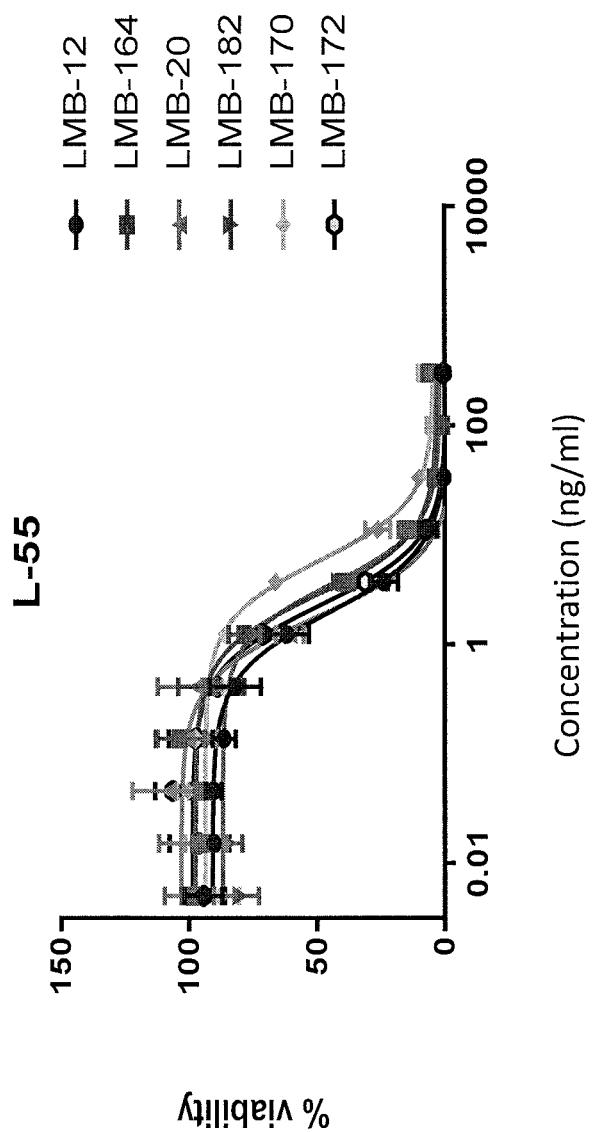
Figure 6D:
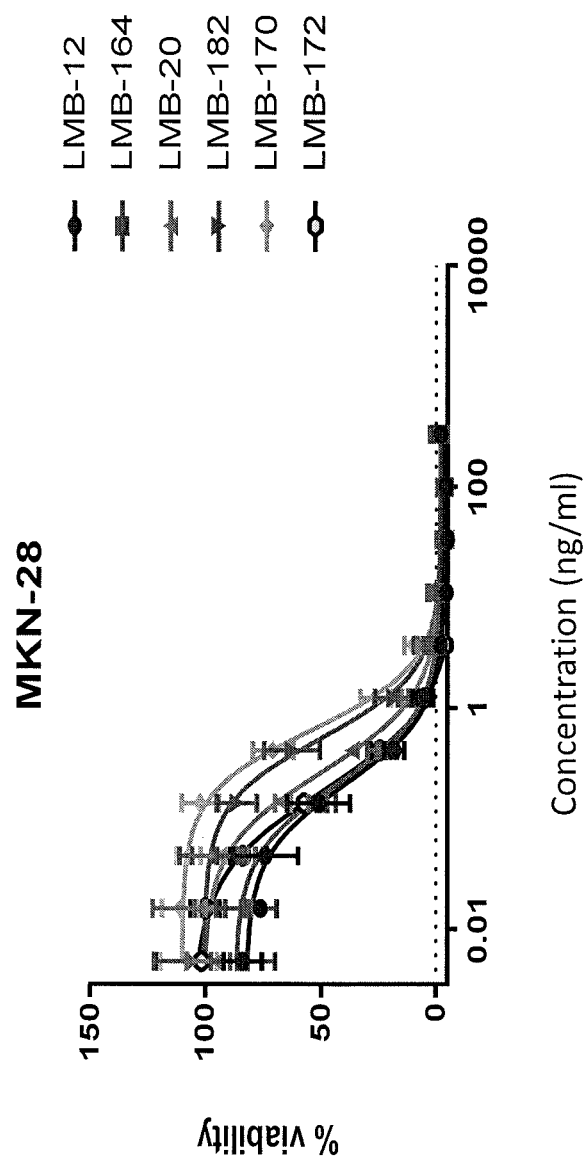

FIG. 5 is an image of a non-reduced SDS-gel including bands indicating the molecular weights for a marker, and for RITs LMB-12, LMB-164, LMB-20, LMB-182, LMB-170, and LMB-172, respectively.

FIGS. 6A-6D depict experimental data illustrating the results of cytotoxicity assays of constructs LMB-12, LMB-164, LMB-20, LMB-182, LMB-170, and LMB-172 on cancer cell lines KLM1 (6A), A431/H9 (6B), L-55 (6C), and MKN-28 (6D), respectively. The Y-axis represents the % of viability of the target cells. The X-axis represents the concentration of immunotoxin in ng/ml.

Figure 7A:
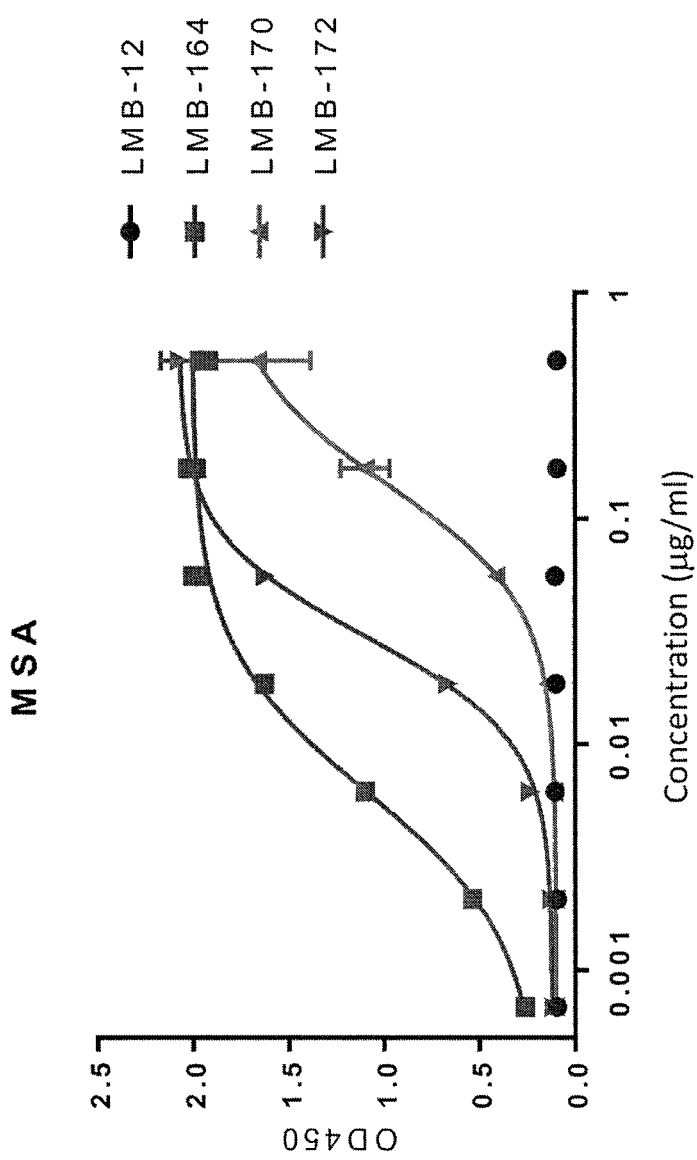

FIG. 7A depicts experimental data illustrating the results of albumin binding assays of LMB-12, LMB-164, LMB-170, and LMB-172 to mouse serum albumin (MSA). The Y-axis represents the optical density at a wavelength of 450 ($OD_{450}$). The X-axis represents the concentration of immunotoxin in μg/ml.

Figure 7B:
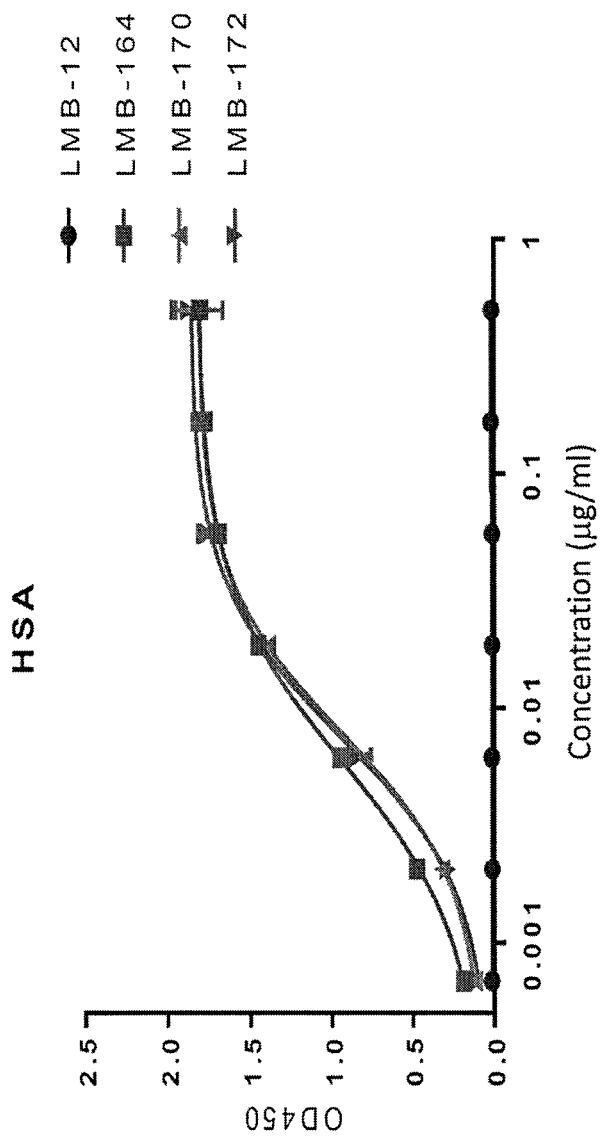

FIG. 7B depicts experimental data illustrating albumin binding assays of LMB-12, LMB-164, LMB-170, and LMB172 to human serum albumin (HSA). The Y-axis represents the optical density at a wavelength of 450 ($OD_{450}$). The X-axis represents the concentration of immunotoxin in μg/ml.

Figure 7C:
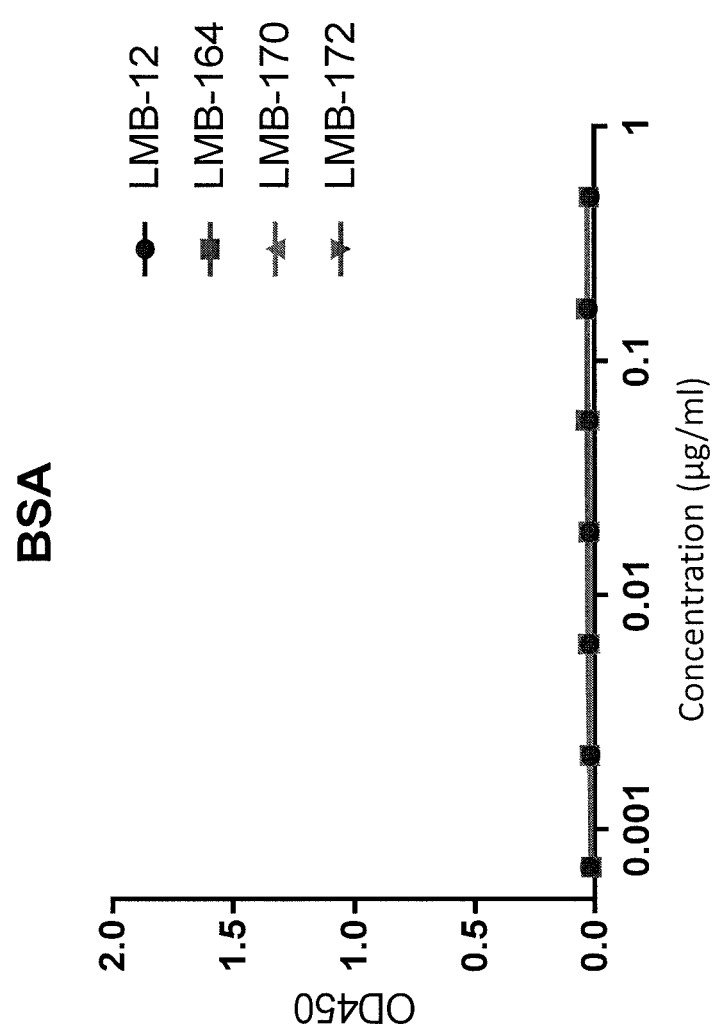

FIG. 7C depicts experimental data illustrating albumin binding assays of LMB-12, LMB-164, LMB-170, and LMB172 to bovine serum albumin (BSA). The Y-axis represents the optical density at a wavelength of 450 ($OD_{450}$). The X-axis represents the concentration of immunotoxin in μg/ml.

FIGS. 8A-8D depict experimental data illustrating the half-life studies and results of LMB-12 (8A), LMB-20 (8B), LMB-164 (8C), and LMB-182 (8D). The half-lives are calculated from blood taken at four various points between 0 and 1500 minutes. The Y-axis axis represents the concentration of immunotoxin in μg/ml. The X-axis represents the number of minutes in the studies.

Figure 8B:
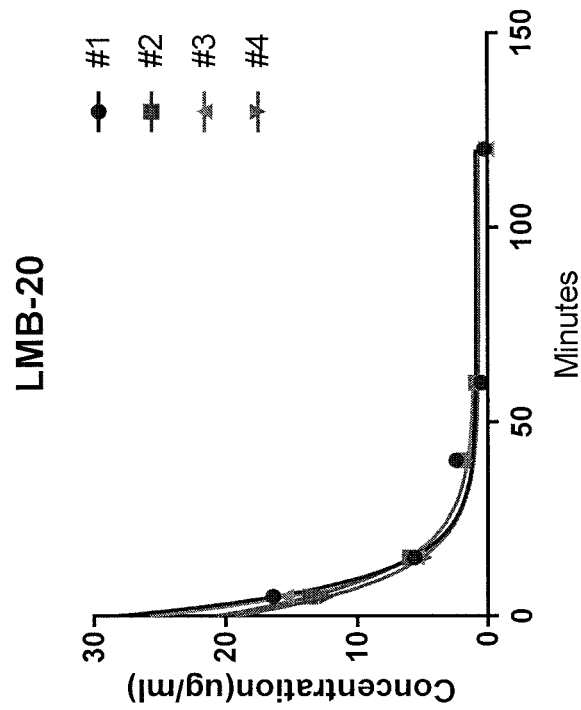
Figure 8A:
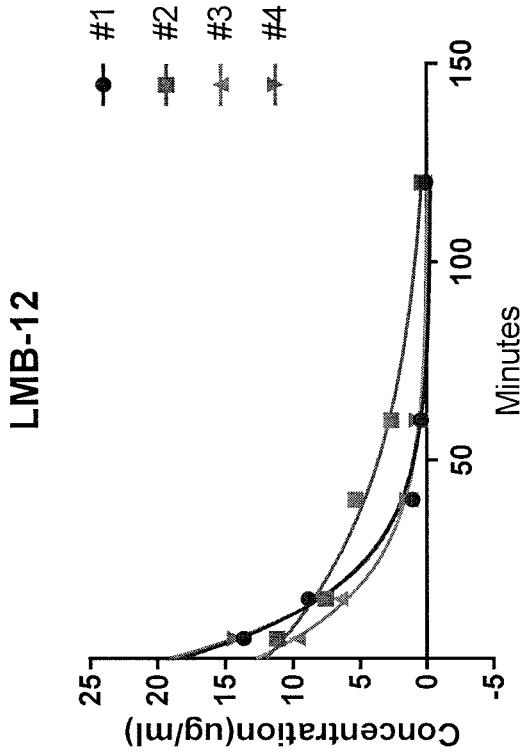
Figure 8C:
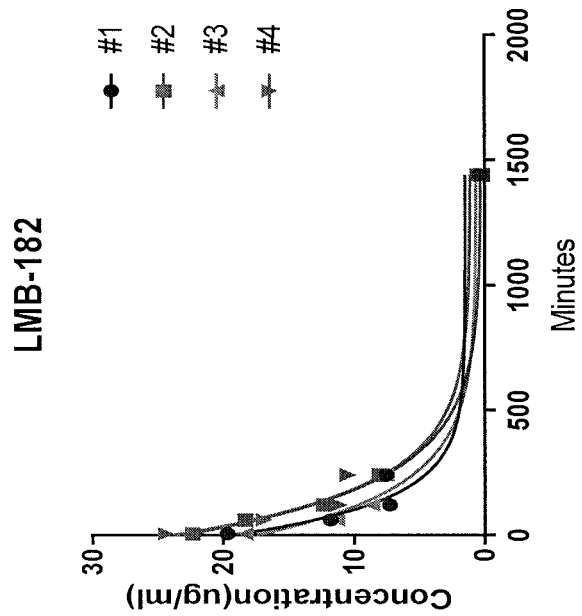
Figure 8D:
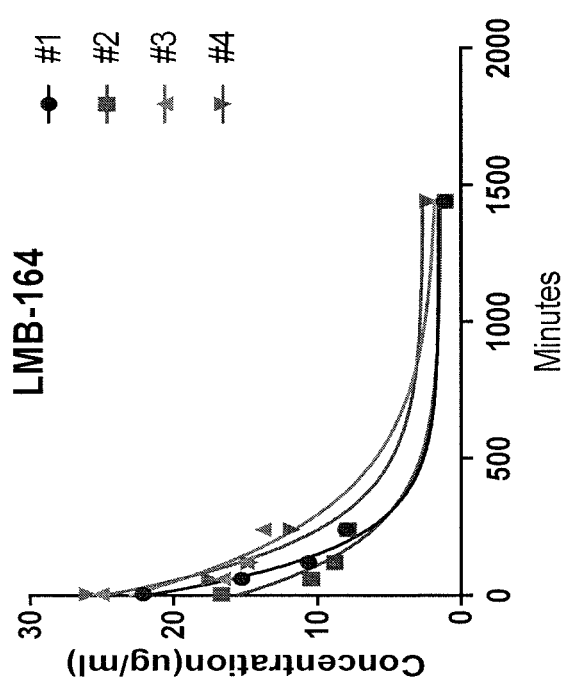
Figure 8F:
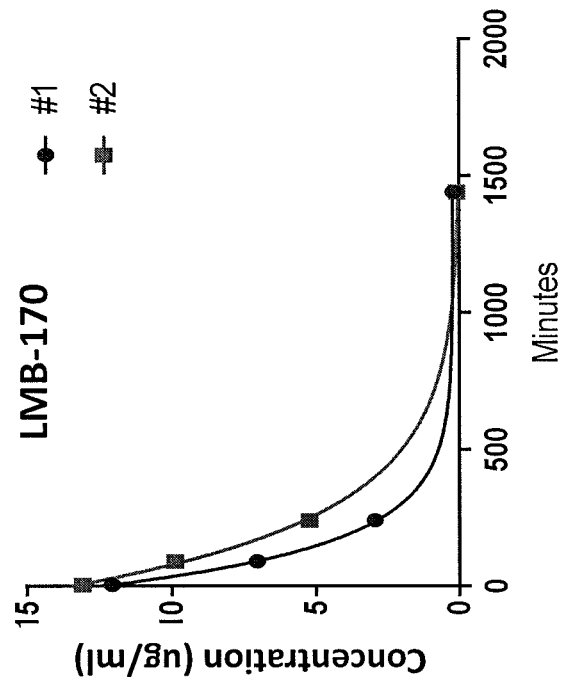
Figure 8E:
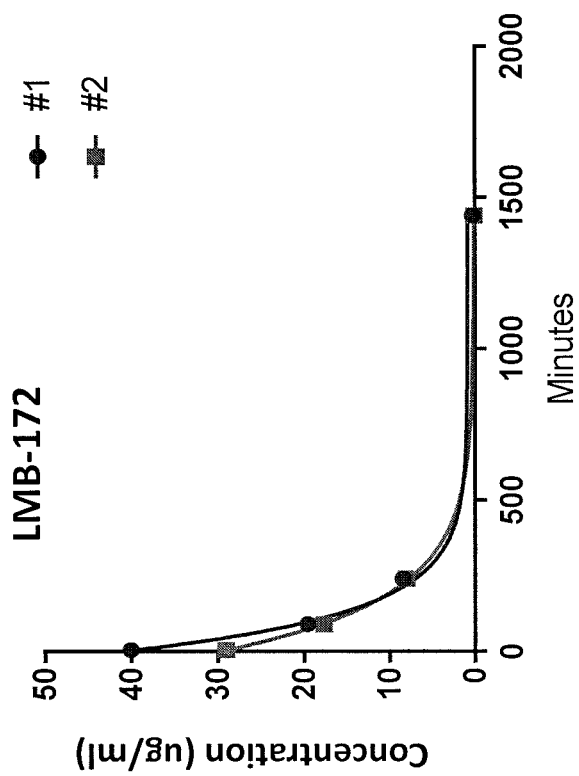

FIGS. 8E-8F depict experimental data illustrating the half-life studies and results of LMB-172 (8E) and LMB-170 (8F). The half-lives are calculated from blood taken at two various points between 0 and 1500 minutes. The Y-axis represents the concentration of immunotoxin in μg/ml. The X-axis represents the number of minutes in the studies.

Figure 9:
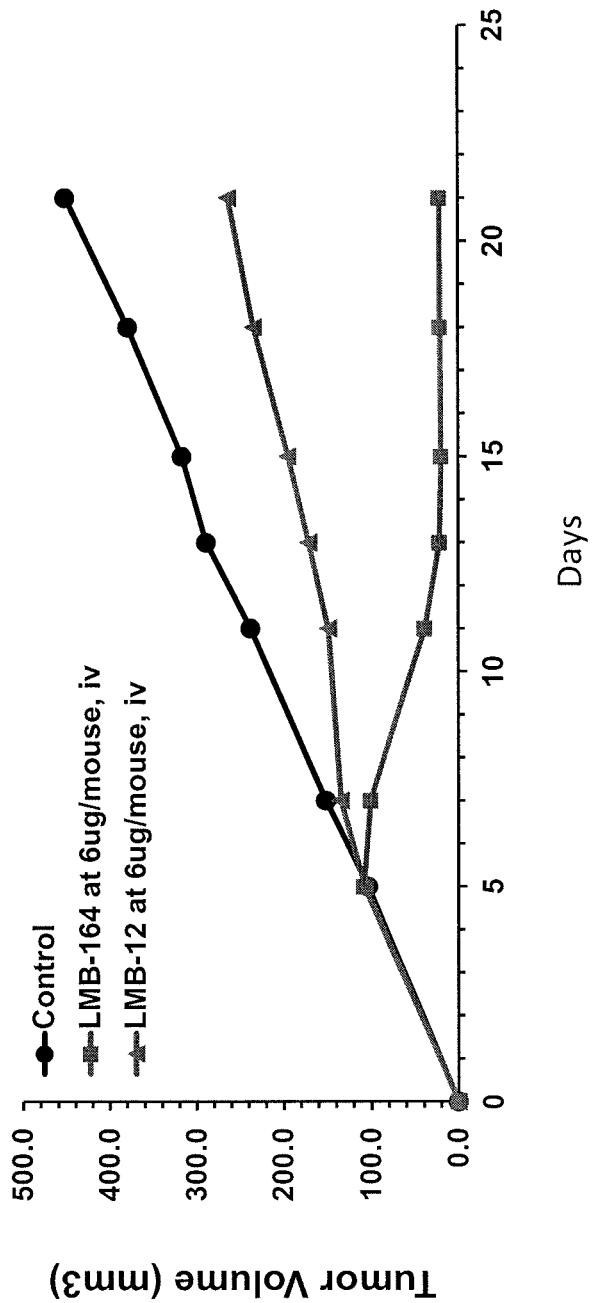

FIG. 9 is a graph depicting the effect on tumor volume of 9 injections of either LMB-164 or LMB-12 in athymic mice bearing KLM1 tumors, a human pancreatic cancer cell line. The number of mice treated was between 5-10. Mice were intravenously injected with 6 μg (per mouse) of either LMB-164 or LMB-12 on days 5, 6, 7, 8, 9, and 12, 13, 14, and 15. The Y-axis represents tumor volume in $mm^3$. The X-axis represents the number of days.

Figure 10:
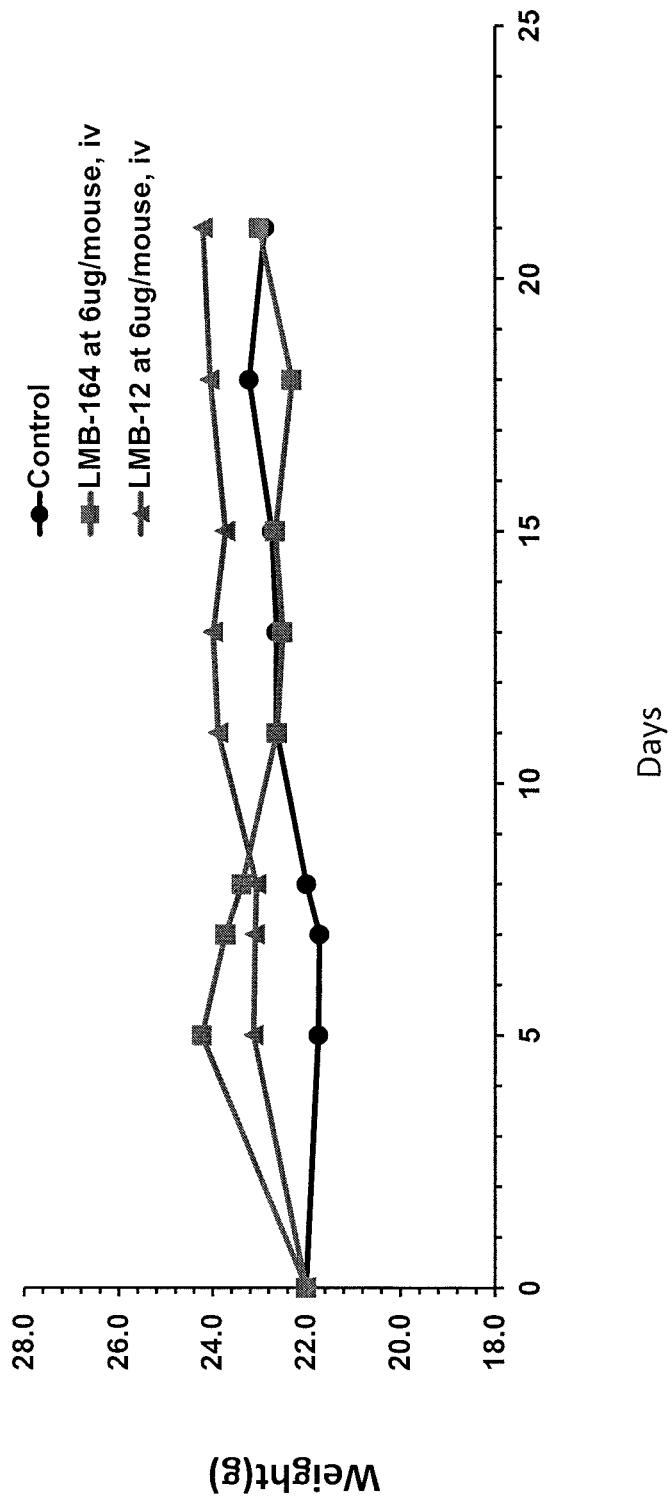

FIG. 10 is a graph depicting the weight of the of the individual mice tested in FIG. 9 following injections of LMB-164 or LMB-12 The Y-axis represents the weight of the mice in grams. The X-axis represents the number of days.

Figure 11:
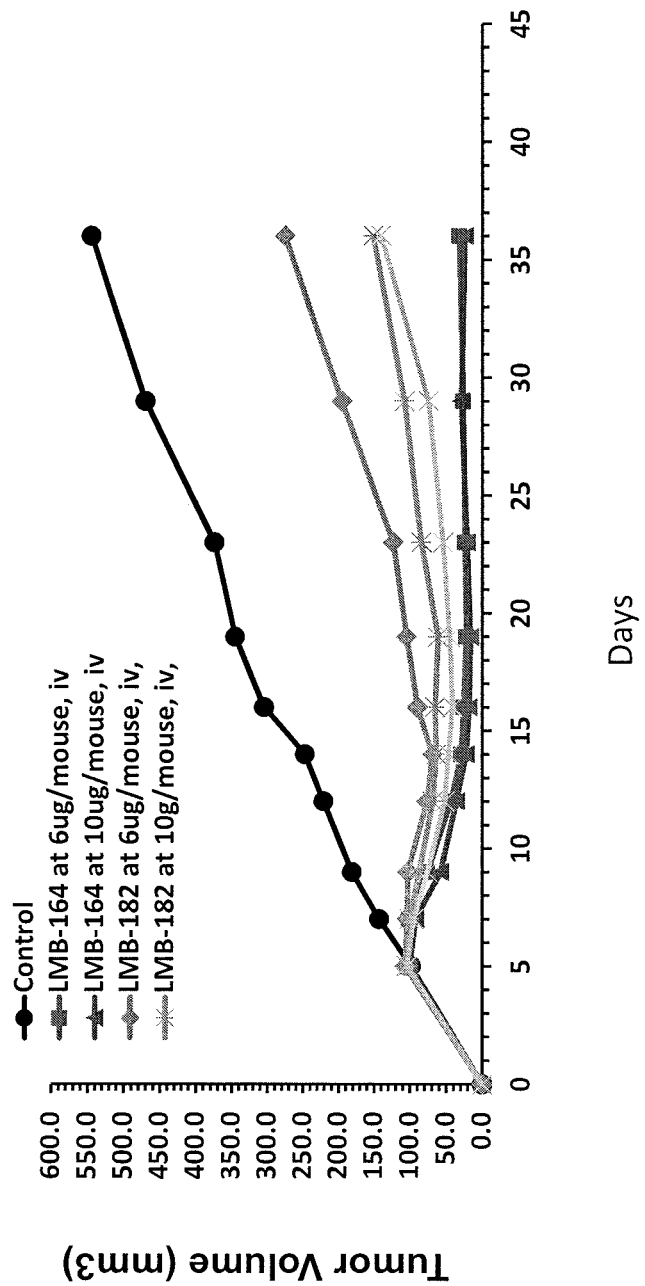

FIG. 11 is a graph depicting the effect of injections of LMB-164 and LMB-182 at varying doses on tumor volume in seven athymic mice bearing KLM1. Mice were intravenously injected with 6 μg of LMB-164 on days 5, 6, 7, 8, 9, 10, and 13, 14, and 15, or 10 μs of LMB-164 on days 5, 6, 7, 8, and 13, 14, and 15. Mice were intravenously injected with 6 μg, 10 μg, or 20 μs of LMB-182 on days 5, 6, 7, 8, 9, 10, and 13, 14, and 15. The Y-axis represents tumor volume in $mm^3$. The X-axis represents the number of days.

FIG. 12A is a schematic of RIT construct a (anti)-Tac-M1-PE38 which includes the Fv of an anti-Tac antibody (which recognizes the human CD25 receptor). The Vh and Vl of the Fv are fused to each other through disulfide bonds formed via cysteine residues (C). The Fv is fused to PE38 via a KASGG linker (SEQ ID NO: 7).

FIG. 12B is a schematic of RIT construct ABD-M1-PE38, ("LMB-167"). LMB-167 is an immunotoxin containing anti-Tac-M1-PE38 construct which includes the Fv of an anti-Tac antibody (which recognizes the human CD25 receptor) fused to the 54 amino acid ABD from *Streptococcus* (SEQ ID NO: 2). The Vh and Vl of the Fv are fused to each other through disulfide bonds formed via cysteine residues (C). ABD is inserted at the amino terminus of the Fv via a 15 amino acid GGGGSGGGGSGGGGSGG ("(G4S)$_3$GG") linker (SEQ ID NO: 35).

FIG. 12C is a schematic of RIT construct M1-PE38-ABD, an anti-Tac-M1-PE38 immunotoxin containing construct which includes the ABD-S from *Streptococcus* (SEQ ID NO: 2). The Vh and Vl of the Fv are fused to each other through disulfide bonds formed via cysteine residues (C). The 54 amino acid ABD-S is inserted near the end of domain III, but before the sequence needed to translocate the immunotoxin to the endoplasmic reticulum (SEQ ID NO: 36).

Figure 13A:
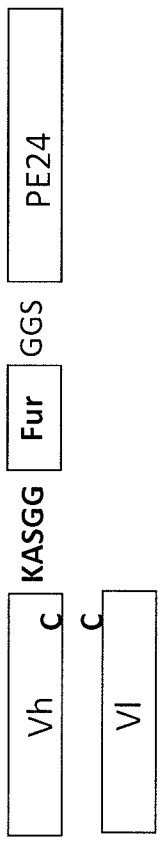

FIG. 13A is a schematic of RIT BM306-dsFv-LRggs, ("LMB-75"). LMB-75 is a PE24 immunotoxin containing construct with a Fv targeted at BCMA on myeloma cells. The Vh and Vl of the Fv are fused to each other through disulfide bonds formed via cysteine residues (C). The Fv is fused to the 11 amino acid Fur via a KASGG linker (SEQ ID NO: 7). Fur, in turn, is fused to PE24 via a 3 amino acid GGS linker (SEQ ID NO: 8).

Figure 13B:
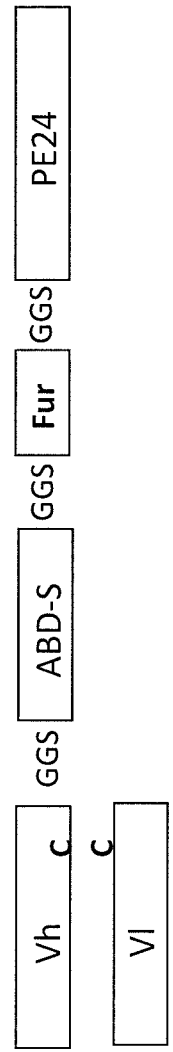

FIG. 13B is a schematic of RIT BM306-ABD-LRggs, ("LMB-162"). LMB-162 is a PE24 immunotoxin containing construct with a Fv targeted at BCMA on myeloma cells which includes the 54 amino acid ABD-S sequence (SEQ ID NO: 2). The Vh and Vl of the Fv are fused to each other through disulfide bonds formed via cysteine residues (C). The Fv is fused to ABD-S via a 3 amino acid GGS linker (SEQ ID NO: 8), which, in turn, is fused to the 11 amino acid Fur via a GGS linker (SEQ ID NO: 8). Fur is fused to PE24 via a GGS linker (SEQ ID NO: 8).

Figure 13C:
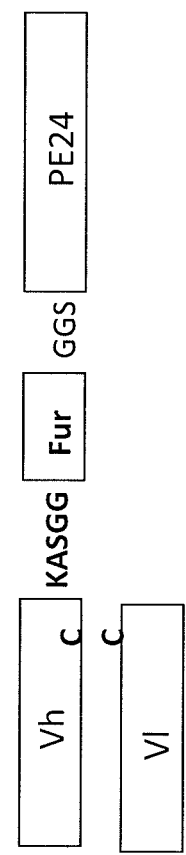

FIG. 13C is a schematic of RIT HA22-dsFv-LRggs, ("LMB-13"). LMB-13 is a PE24 immunotoxin containing construct with a Fv targeted at CD22 on leukemia cells. The Vh and Vl of the Fv are fused to each other through disulfide bonds formed via cysteine residues (C). The Fv is fused to the 11 amino acid Fur via a KASGG linker (SEQ ID NO: 7). Fur, in turn, is fused to PE24 via a 3 amino acid GGS linker (SEQ ID NO: 8).

Figure 13D:
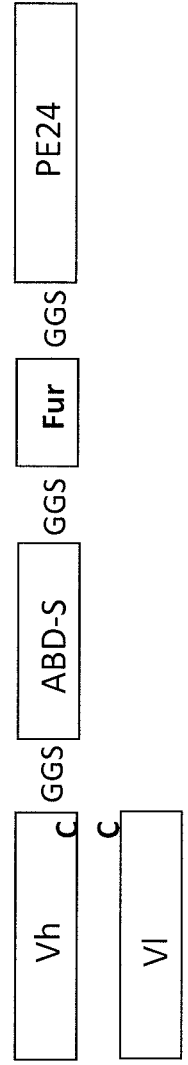

FIG. 13D is a schematic of RIT HA22-ABD-LRggs, ("LMB-196"). LMB-196 is a PE24 immunotoxin containing construct with a Fv targeted at CD22 on leukemia cells which includes the 54 amino acid ABD-S sequence (SEQ ID NO: 2). The Vh and Vl of the Fv are fused to each other through disulfide bonds formed via cysteine residues (C). The Fv is fused to ABD-S via a 3 amino acid GGS linker (SEQ ID NO: 8), which, in turn, is fused to the 11 amino acid Fur via a GGS linker (SEQ ID NO: 8). Fur is fused to PE24 via a GGS linker (SEQ ID NO: 8).

Figure 14:
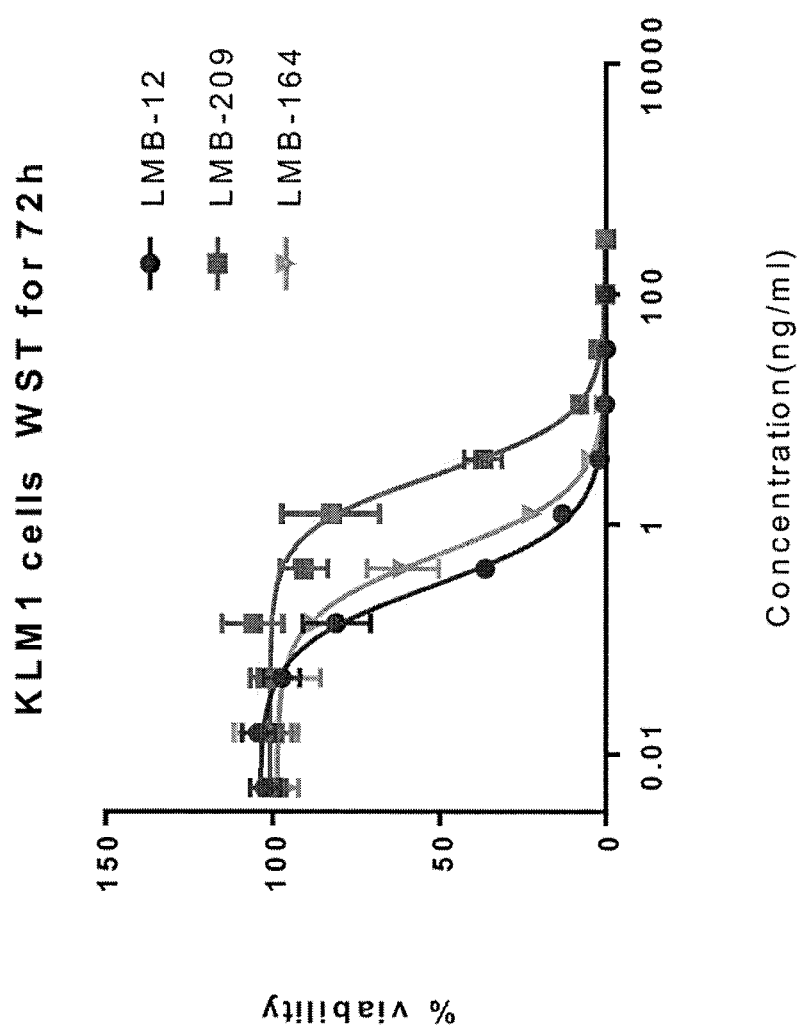

FIG. 14 is a graph depicting the results of toxicity assays of LMB-12, LMB-209 and LMB-164 on KLM1 cell lines. The Y-axis represents % viability. The X-axis represents the concentration of immunotoxin in ng/ml.

Figure 15A:
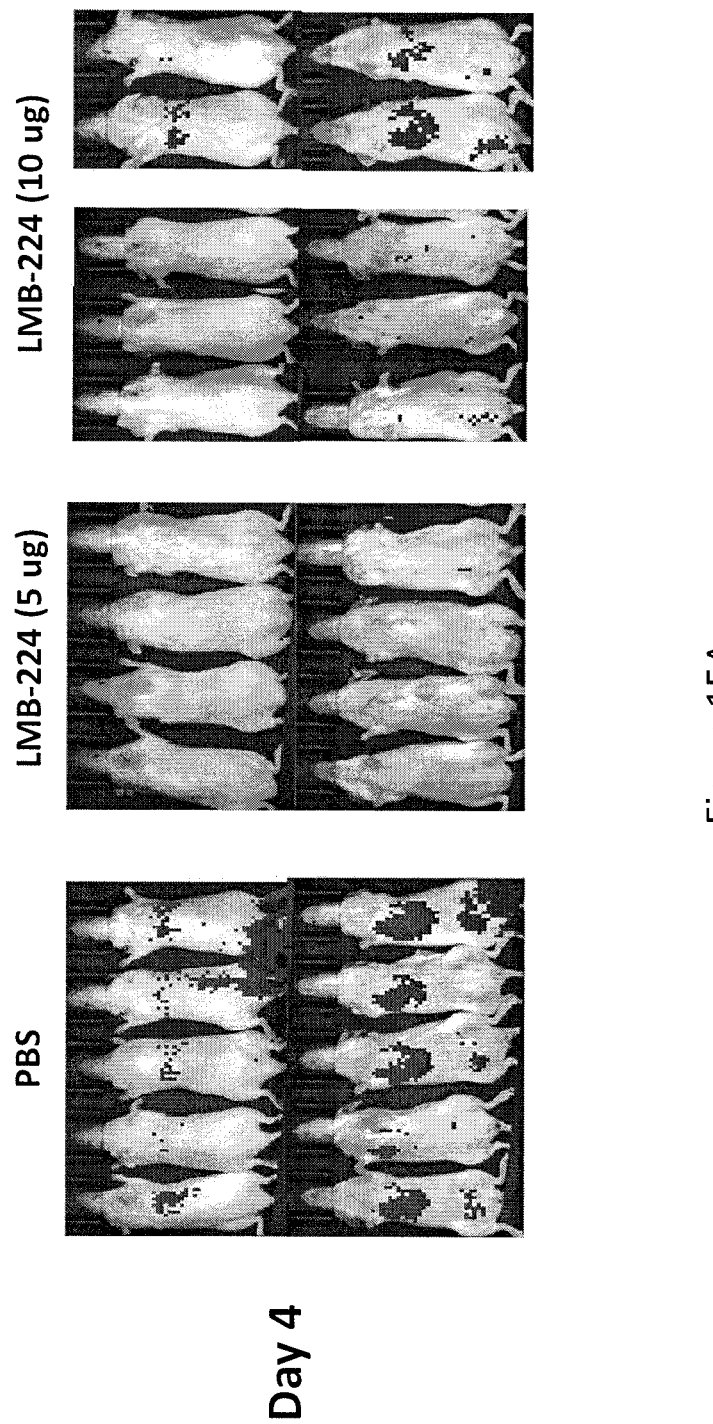
Figure 15B:
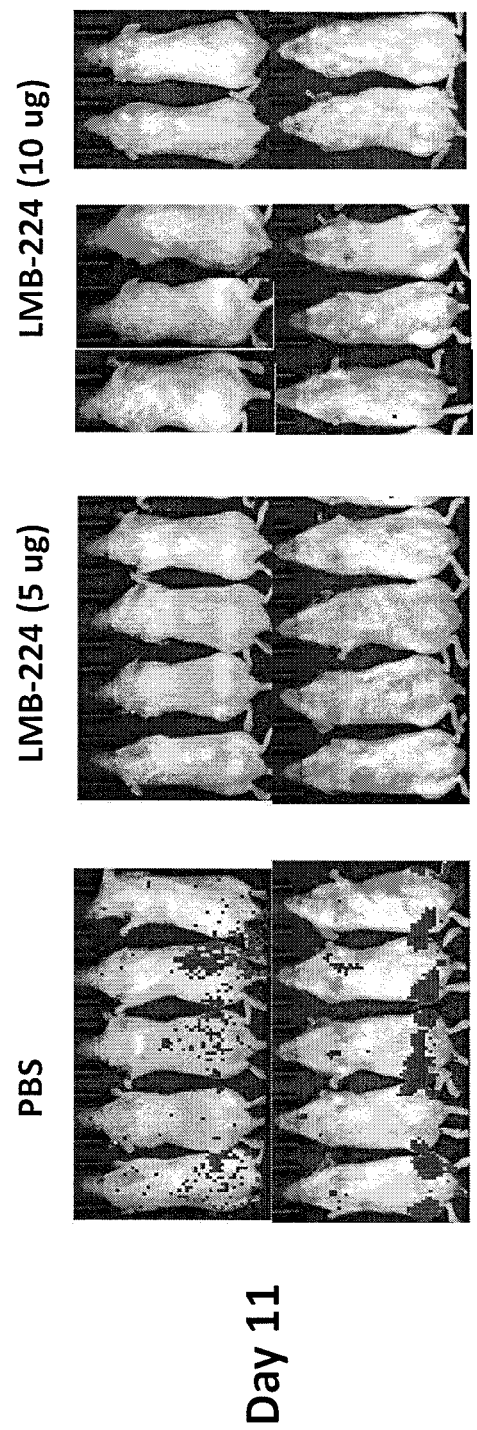
Figure 15C:
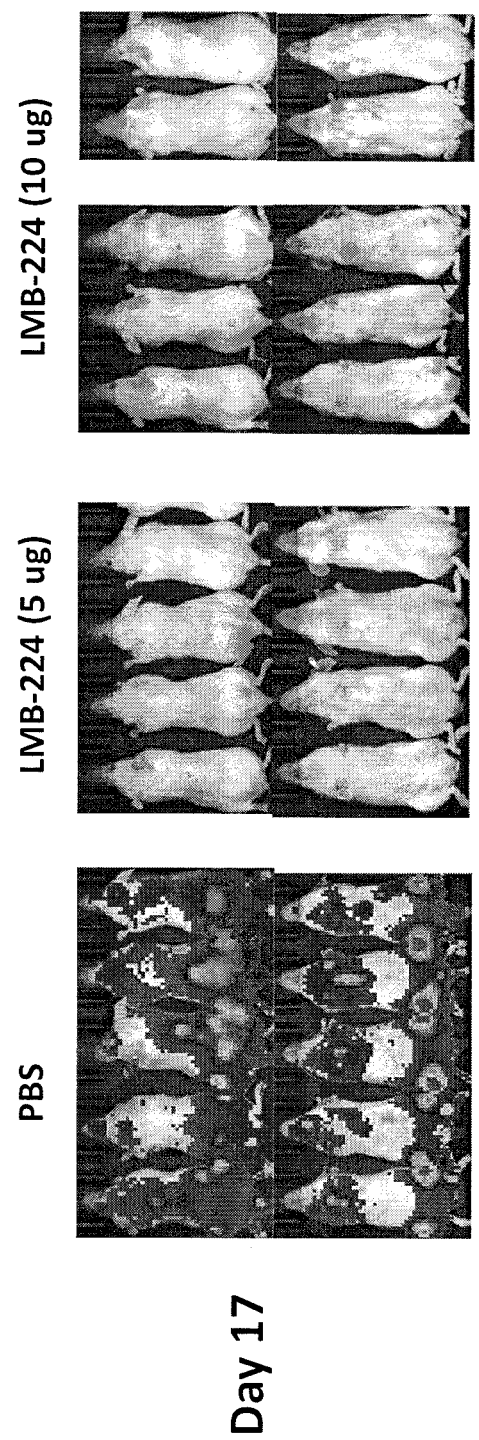

FIGS. 15A-C are a series of bioluminescence imaging photographs showing the tumor burden in immunodeficient NSG mice which were intravenously injected with H929-luc-GFP cells. Mice were treated intravenously with either phosphate buffered saline (PBS) (control), 5 µg of LMB-224, or 10 µs of LMB-224. Bioluminescence imaging photographs were taken on days 4, 11, and 17.

FIG. 15A shows the bioluminescence imaging photographs taken on day 4 right before the treatment started. The shaded areas on the mice indicate tumor burden. Mice were treated intravenously with either phosphate buffered saline (PBS) (control), 5 µg of LMB-224, or 10 µg of LMB-224 every other day for 5 doses (QODX5).

FIG. 15B shows the bioluminescence imaging photographs taken on day 11. The shaded areas on the mice indicate tumor burden. Compared to the control mice, the mice that were administered LMB-224 (both 5 and 10 µg) show almost no tumor burden.

FIG. 15C shows the bioluminescence imaging photographs taken on day 17. The shaded areas on the mice indicate tumor burden. Compared to the control mice, the mice that were administered LMB-224 (both 5 and 10 µg) continued to show complete remission and remained tumor free after the treatment was complete.

Figure 16A:
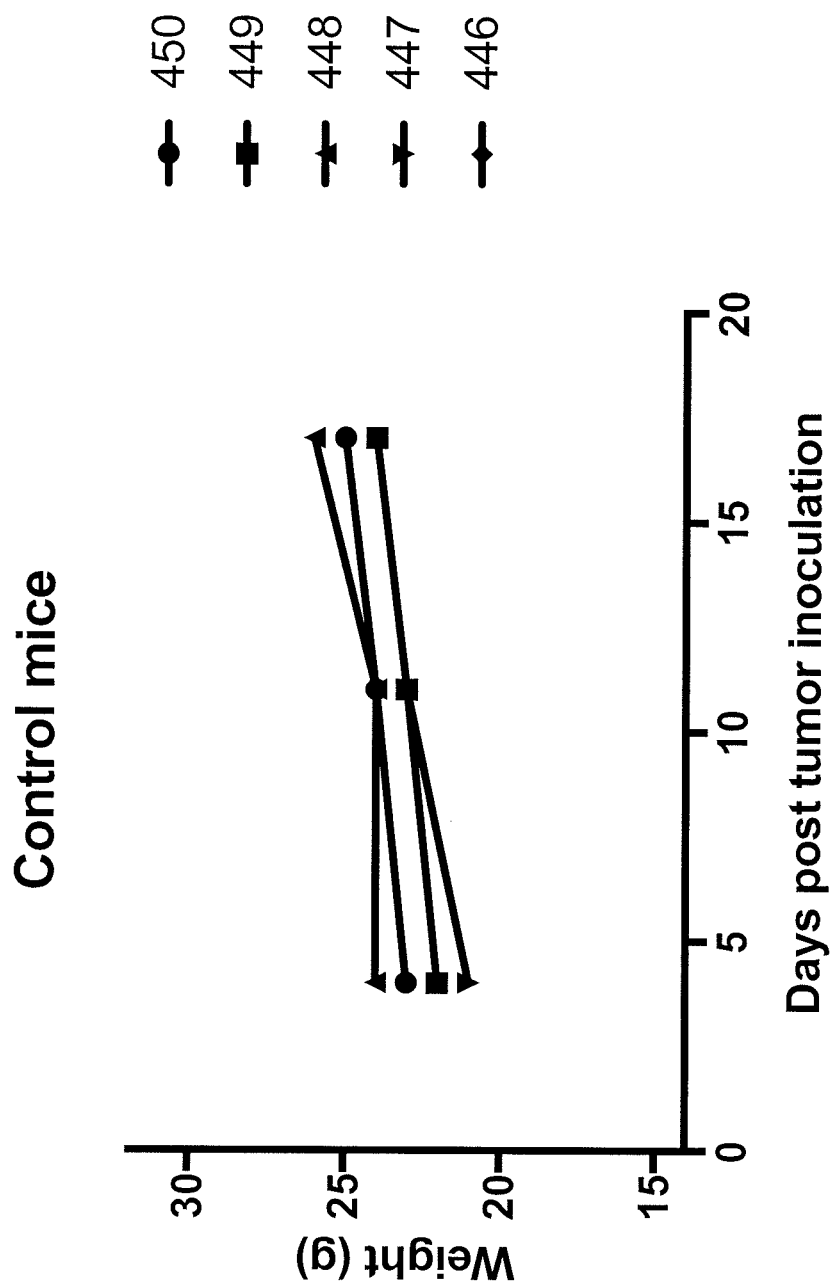

FIG. 16A is a graph showing weights of individual mice in the control (PBS) group. Individual mice are labeled by number. The X-axis is the number of days post tumor inoculation. The Y-axis is the weight of the mice in grams.

Figure 16B:
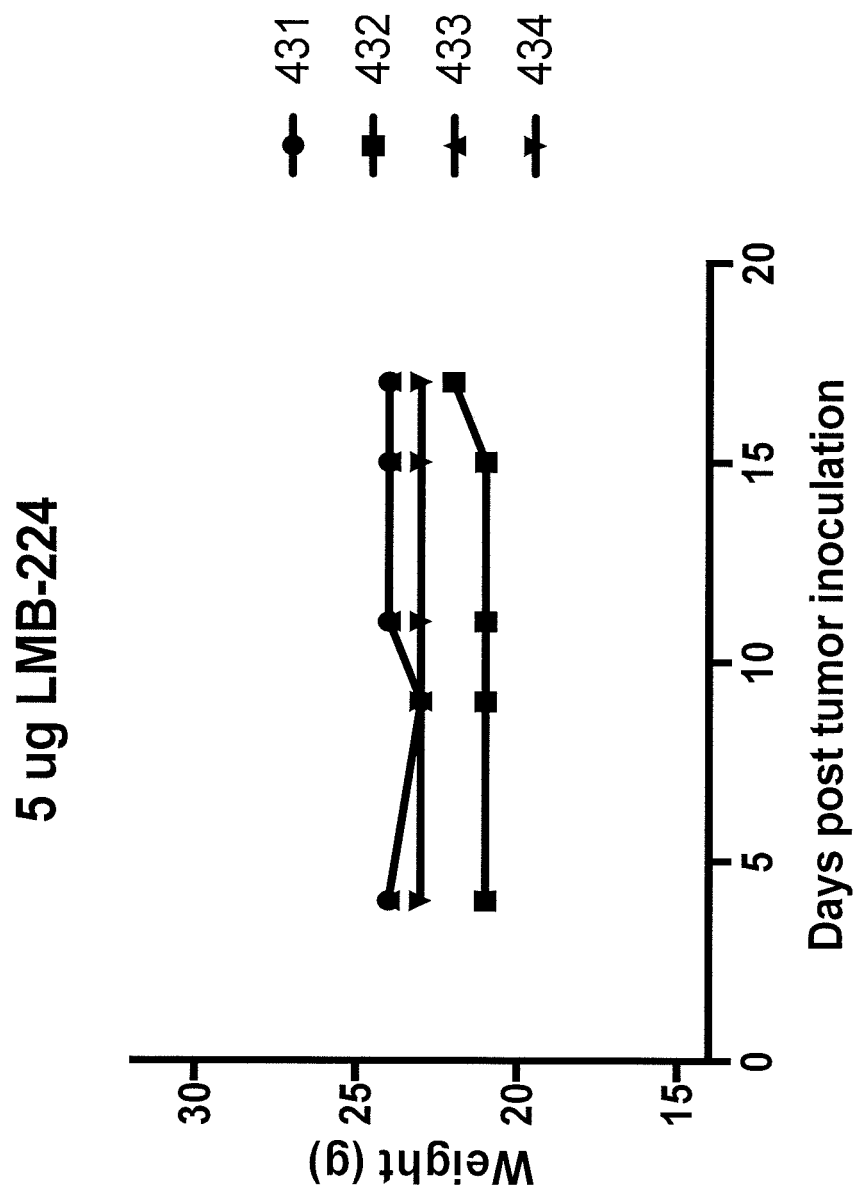

FIG. 16B is a graph showing weights of individual mice in the treatment group administered 5 µg of LMB-224. Individual mice are labeled by number. The X-axis is the number of days post tumor inoculation. The Y-axis is the weight of the mice in grams. The graph indicates that no significant weight loss occurred in this group due to treatment associated toxicity.

Figure 16C:
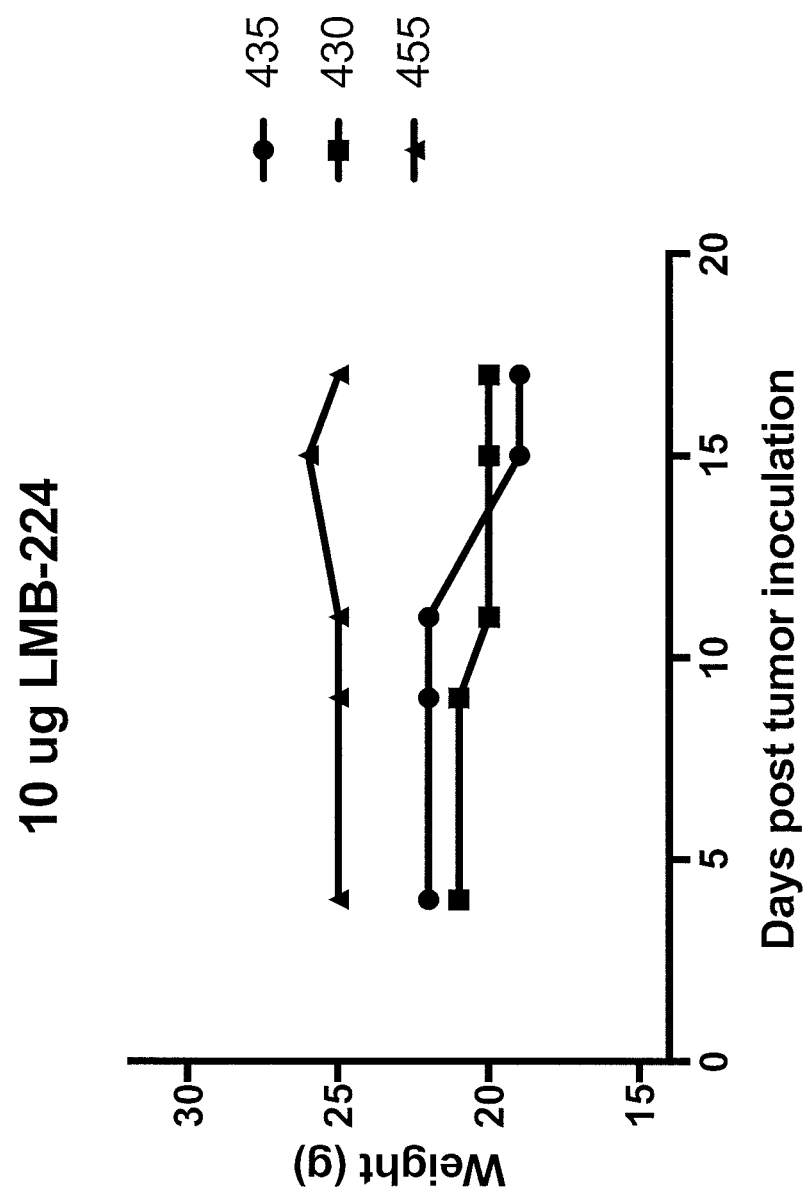

FIG. 16C is a graph showing weights of individual mice in the treatment group administered 10 µg of LMB-224. Individual mice are labeled by number. The X-axis is the number of days post tumor inoculation. The Y-axis is the weight of the mice in grams. The graph indicates that no significant weight loss occurred in this group due to treatment associated toxicity.

Figure 17A:
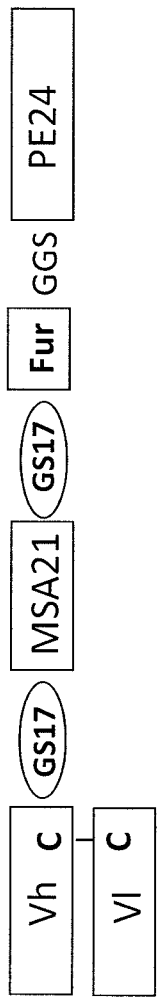

FIG. 17A is a schematic of RIT construct BM306-MSA21-LRggs, ("LMB-173"). LMB-173 is a PE24 immunotoxin construct with a Fv targeting BCMA on myeloma cells based on parent LMB-75. The Vh and Vl of the Fv are fused to each other through disulfide bonds formed via cysteine residues (C). LMB-173 has inserted a 115 amino acid single domain antibody from Llama named MSA21 which is attached to the Fv and to Fur via 17 amino acid peptide linkers GS17 (SEQ ID NO: 35). Fur is fused to PE24 via a 3 amino acid GGS linker (SEQ ID NO: 8).

Figure 17B:
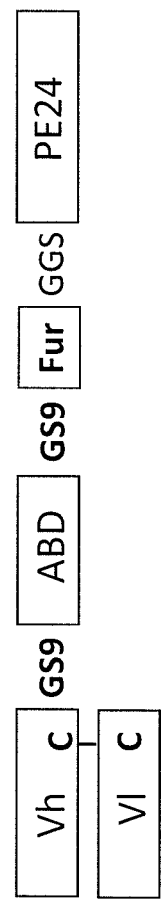

FIG. 17B is a schematic of RIT BM306-lin-ABD-lin, ("LMB-224"). LMB-224 is a PE24 immunotoxin containing construct with a Fv targeting BCMA on myeloma cells which includes the 54 amino acid ABD-S sequence (SEQ ID NO: 2). The Vh and Vl of the Fv are fused to each other through disulfide bonds formed via cysteine residues (C). The Fv is fused to ABD-S via a 9 amino acid GS9 peptide linker (SEQ ID NO: 38), which, in turn, is fused to the 11 amino acid Fur via a 9 amino acid GS9 peptide linker (SEQ ID NO: 38). Fur is fused to PE24 via a 3 amino acid GGS linker (SEQ ID NO: 8).

Figure 17C:
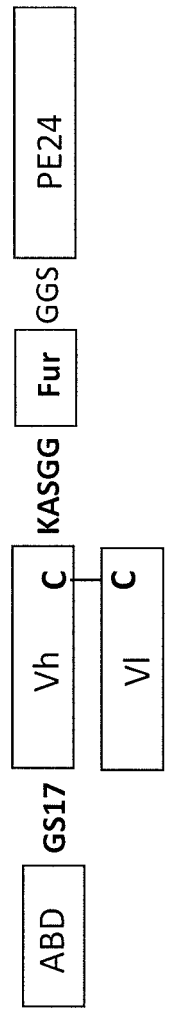

FIG. 17C is a schematic of RIT BM306-ABD-lin-Vh, ("LMB-235"). LMB-235 is a PE24 immunotoxin construct with a Fv targeted at BCMA on myeloma cells which includes the 54 amino acid ABD-S sequence (SEQ ID NO: 2) inserted before the Fv. The ABD sequence is fused to the amino terminus of the heavy chain of the Fv via a 17 amino acid peptide linker GS17 (SEQ ID NO: 35). The Vh and Vl of the Fv are fused to each other through disulfide bonds formed via cysteine residues (C). The Fv is fused to the 11 amino acid Fur via a 5 amino acid KASGG peptide linker (SEQ ID NO: 7). Fur is fused to PE24 via a 3 amino acid GGS linker (SEQ ID NO: 8).

Figure 17D:
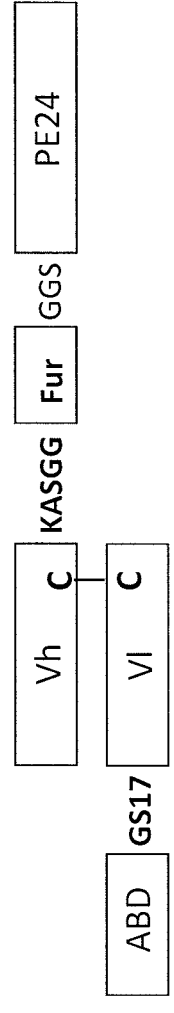

FIG. 17D is a schematic of RIT BM306-ABD-lin-Vl, ("LMB-237"). LMB-237 is a PE24 immunotoxin construct with a Fv targeted at BCMA on myeloma cells which includes the 54 amino acid ABD-S sequence (SEQ ID NO: 2) inserted before the Fv. The ABD sequence is fused to the amino terminus of the light chain of the Fv via a 17 amino acid peptide linker GS17 (SEQ ID NO: 35). The Vh and Vl of the Fv are fused to each other through disulfide bonds formed via cysteine residues (C). The Fv is fused to the 11 amino acid Fur via a 5 amino acid KASGG peptide linker (SEQ ID NO: 7). Fur is fused to PE24 via a 3 amino acid GGS linker (SEQ ID NO: 8).

DETAILED DESCRIPTION OF THE INVENTION

*Pseudomonas* exotoxin A ("PE") is a bacterial toxin (molecular weight 66 kD) secreted by *Pseudomonas aeruginosa*. The native, wild-type PE sequence (SEQ ID NO: 1) is set forth in U.S. Pat. No. 5,602,095, which is incorporated herein by reference. Native, wild-type PE includes three structural domains that contribute to cytotoxicity. Domain Ia (amino acids 1-252) mediates cell binding, domain II (amino acids 253-364) mediates translocation into the cytosol, and domain III (amino acids 400-613) mediates ADP ribosylation of elongation factor 2. While the structural boundary of domain III of PE is considered to start at residue 400, it is contemplated that domain III may require a segment of domain Ib to retain ADP-ribosylating activity. Accordingly, functional domain III is defined as residues 395-613 of PE. The function of domain Ib (amino acids 365-399) remains undefined. Without being bound by a particular theory or mechanism, it is believed that the cytotoxic activity of PE occurs through the inhibition of protein synthesis in eukaryotic cells, e.g., by the inactivation of the ADP-ribosylation of elongation factor 2 (EF-2).

Substitutions of PE are defined herein by reference to the amino acid sequence of PE. Thus, substitutions of PE are described herein by reference to the amino acid residue present at a particular position, followed by the position number, followed by the amino acid with which that residue has been replaced in the particular substitution under discussion. In this regard, the positions of the amino acid sequence of a particular embodiment of a PE are referred to herein as the positions as defined by SEQ ID NO: 1. When the positions are as defined by SEQ ID NO: 1, then the actual positions of the amino acid sequence of a particular embodiment of a PE are defined relative to the corresponding positions of SEQ ID NO: 1, and the positions as defined by SEQ ID NO: 1 may be different than the actual positions in the particular embodiment of PE under discussion. Thus, for example, substitutions refer to a replacement of an amino acid residue in the amino acid sequence of a particular embodiment of a PE corresponding to the indicated position of the 613-amino acid sequence of SEQ ID NO: 1 with the understanding that the actual positions in the respective amino acid sequences may be different. For example, when the positions are as defined by SEQ ID NO: 1, the term "R490" refers to the arginine normally present at position 490 of SEQ ID NO: 1, "R490A" indicates that the arginine normally present at position 490 of SEQ ID NO: 1 is replaced by an alanine, while "K590Q" indicates that the lysine normally present at position 590 of SEQ ID NO: 1 has been replaced with a glutamine. In the event of multiple substitutions at two or more positions, the two or more substitutions may be the same or different, i.e., each amino acid residue of the two or more amino acid residues being substituted can be substituted with the same or different amino acid residue unless explicitly indicated otherwise.

The terms "*Pseudomonas* exotoxin" and "PE" as used herein include PE that has been modified from the native protein to reduce or to eliminate immunogenicity. Such modifications may include, but are not limited to, elimination of domain Ia, various amino acid deletions in domains Ib, II, and III, single amino acid substitutions and the addition of one or more sequences at the carboxyl terminus such as DEL and REDL (SEQ ID NO: 3). See Siegall et al., *J. Biol. Chem.*, 264: 14256-14261 (1989). In an embodiment, the PE may be a cytotoxic fragment of native, wild-type PE. Cytotoxic fragments of PE may include those which are cytotoxic with or without subsequent proteolytic or other processing in the target cell (e.g., as a protein or pre-protein). In a preferred embodiment, the cytotoxic fragment of PE retains at least about 20%, preferably at least about 40%, more preferably at least about 50%, even more preferably 75%, more preferably at least about 90%, and still more preferably at least about 95% of the cytotoxicity of native PE. In particularly preferred embodiments, the cytotoxic fragment has at least the cytotoxicity of native PE, and preferably has increased cytotoxicity as compared to native PE.

Modified PE that reduces or eliminates immunogenicity includes, for example, PE4E, PE40, PE38, PE25, PE38QQR, PE38KDEL, PE-LR, PE35, and PE24. In an embodiment, the PE may be any of PE4E, PE40, PE38, PE25, PE38QQR (in which PE38 has the sequence QQR added at the C-terminus), PE38KDEL (in which PE38 has the sequence KDEL (SEQ ID NO: 4) added at the C-terminus), PE-LR (resistance to lysosomal degradation), PE35, and PE24.

In an embodiment, the PE is PE24. PE24 contains only functional domain III (residues 395-613) of PE.

In an embodiment, the PE has been modified to reduce immunogenicity by deleting domain Ia as described in U.S. Pat. No. 4,892,827, which is incorporated herein by reference. The PE may also be modified by substituting certain residues of domain Ia. In an embodiment, the PE may be PE4E, which is a substituted PE in which domain Ia is present but in which the basic residues of domain Ia at positions 57, 246, 247, and 249 are replaced with acidic residues (e.g., glutamic acid), as disclosed in U.S. Pat. No. 5,512,658, which is incorporated herein by reference.

PE40 is a truncated derivative of PE (Pai et al., *Proc. Nat'l Acad. Sci. USA*, 88: 3358-62 (1991) and Kondo et al., *Biol. Chem.*, 263: 9470-9475 (1988)). PE35 is a 35 kD carboxyl-terminal fragment of PE in which amino acid residues 1-279 have been deleted and the molecule commences with a Met at position 280 followed by amino acids 281-364 and 381-613 of native PE. PE35 and PE40 are disclosed, for example, in U.S. Pat. Nos. 5,602,095 and 4,892,827, each of which is incorporated herein by reference. PE25 contains the 11-residue fragment from domain II and all of domain III. In some embodiments, the PE contains only domain III.

In an embodiment, the PE is PE38. PE38 contains the translocating and ADP ribosylating domains of PE but not the cell-binding portion (Hwang J. et al., *Cell*, 48: 129-136 (1987)). PE38 is a truncated PE pro-protein composed of amino acids 253-364 and 381-613 which is activated to its cytotoxic form upon processing within a cell (see e.g., U.S. Pat. No. 5,608,039, which is incorporated herein by reference, and Pastan et al., *Biochim. Biophys. Acta*, 1333: C1-C6 (1997)).

In another embodiment, the PE is PE-LR. PE-LR contains a deletion of domain II except for a furin cleavage sequence (FCS) corresponding to amino acid residues 274-284 of SEQ ID NO: 1 (RHRQPRGWEQL (SEQ ID NO: 5)) and a deletion of amino acid residues 365-394 of domain Ib. Thus, PE-LR contains amino acid residues 274-284 and 395-613 of SEQ ID NO: 1. PE-LR is described in U.S. Pat. No. 8,871,906, which is incorporated herein by reference. The PE-LR may, optionally, additionally comprise a GGS linking peptide between the FCS and amino acid residues 395-613 of SEQ ID NO: 1.

As noted above, alternatively or additionally, some or all of domain Ib may be deleted with the remaining portions joined by a bridge or directly by a peptide bond. Alternatively or additionally, some of the amino portion of domain II may be deleted. Alternatively or additionally, the C-terminal end may contain the native sequence of residues 609-613 (REDLK) (SEQ ID NO: 6), or may contain a variation that may maintain the ability of the PE to translocate into the cytosol, such as KDEL (SEQ ID NO: 4) or REDL (SEQ ID NO: 3) and repeats of these sequences. See, e.g., U.S. Pat. Nos. 5,854,044; 5,821,238; and 5,602,095 and International Patent Application Publication WO 1999/051643, which are incorporated herein by reference. Any form of PE in which immunogenicity has been eliminated or reduced can be used in combination with any of the albumin binding domains described herein so long as it remains capable of cytotoxicity to targeted cells, e.g., by translocation and EF-2 ribosylation in a targeted cell.

Immunotoxin molecules may have a short half-life which may make it necessary to administer large amounts of immunotoxin to obtain high blood levels of immunotoxin so that enough immunotoxin can enter tumors and kill tumor cells. High blood levels of immunotoxin may, undesirably, cause non-specific toxicities. It has been discovered that the addition of an albumin binding domain (ABD) to the immunotoxin molecule may ameliorate some or all of these shortcomings. The inventive molecules may provide any one or more of the following advantages: (i) high cytotoxicity; (ii) high anti-tumor activity; and (iii) a high yields. Alternatively or additionally, the inventive molecules may also provide a longer half-life as compared to immunotoxin molecules which lack an ABD. The insertion of the ABD into the inventive molecule may, advantageously, not reduce or eliminate the cytotoxic activity of the molecule. Without being bound to a particular theory or mechanism, it is believed that the ABD causes the inventive molecules to bind to serum albumin, and because serum albumin has a long half-life, binding to albumin may reduce or prevent the rapid degradation of the molecules and enhance their antitumor activity. Accordingly, the inventive molecules may kill target cells and/or achieve therapeutic efficacy with smaller dosages.

An embodiment of the invention provides a molecule (e.g., a chimeric molecule) comprising: (a) a first domain, which comprises a targeting moiety, wherein the targeting moiety is not an affibody; (b) a second domain, which comprises an albumin binding domain (ABD), (c) a third domain, which comprises a furin cleavage sequence ("FCS") which FCS is cleavable by furin; and (d) a fourth domain, which comprises an optionally substituted Domain III from *Pseudomonas* exotoxin A ("PE").

The term "targeting moiety" as used herein, refers to any molecule or agent that specifically recognizes and binds to a cell-surface marker, such that the targeting moiety directs the delivery of the inventive chimeric molecule to a population of cells on which surface the receptor is expressed. Targeting moieties include, but are not limited to, antibodies (e.g., monoclonal antibodies), or fragments thereof, peptides, hormones, growth factors, cytokines, and any other natural or non-natural ligands. In an embodiment of the invention, the targeting moiety is not an affibody. The practice of conjugating compounds, e.g., inventive PEs, to targeting moieties is known in the art.

The term "antibody," as used herein, refers to whole (also known as "intact") antibodies or antigen binding portions thereof that retain antigen recognition and binding capability. The antibody or antigen binding portions thereof can be a naturally-occurring antibody or antigen binding portion thereof, e.g., an antibody or antigen binding portion thereof isolated and/or purified from a mammal, e.g., mouse, rabbit, goat, horse, chicken, hamster, human, etc. The antibody or antigen binding portion thereof can be in monomeric or polymeric form. Also, the antibody or antigen binding portion thereof can have any level of affinity or avidity for the cell surface marker. Desirably, the antibody or antigen binding portion thereof is specific for the cell surface marker, such that there is minimal cross-reaction with other peptides or proteins.

The antibody may be monoclonal or polyclonal and of any isotype, e.g., IgM, IgG (e.g. IgG, IgG2, IgG3 or IgG4), IgD, IgA or IgE. Complementarity determining regions (CDRs) of an antibody or single chain variable fragments (Fvs) of an antibody against a target cell surface marker can be grafted or engineered into an antibody of choice to confer specificity for the target cell surface marker upon that antibody. For example, the CDRs of an antibody against a target cell surface marker can be grafted onto a human antibody framework of a known three dimensional structure to form an antibody that may raise little or no immunogenic response when administered to a human. In a preferred embodiment, the targeting moiety is a monoclonal antibody.

The antigen binding portion can be any portion that has at least one antigen binding site, such as, e.g., the variable regions or CDRs of the intact antibody. Examples of antigen binding portions of antibodies include, but are not limited to, a heavy chain, a light chain, a variable or constant region of a heavy or light chain, a single chain variable fragment (scFv), or an Fc, Fab, Fab', Fv, or $F(ab)_2$' fragment; single domain antibodies (see, e.g., Wesolowski, *Med Microbiol Immunol.,* 198(3): 157-74 (2009); Saerens et al., *Curr. Opin. Pharmacol.,* 8(5):6 00-8 (2008); Harmsen and de Haard, *Appl. Microbiol. Biotechnol.,* 77(1): 13-22 (2007), helix-stabilized antibodies; triabodies; diabodies; single-chain antibody molecules ("scFvs"); disulfide stabilized antibodies ("dsFvs"), and domain antibodies ("dAbs").

Methods of testing antibodies or antigen binding portions thereof for the ability to bind to any cell surface marker are known in the art and include any antibody-antigen binding assay, such as, for example, radioimmunoassay (RIA), ELISA, Western blot, immunoprecipitation, and competitive inhibition assays (see, e.g., Kenneth Murphy (ed.), *Janeway's Immunobiology,* 8th Ed., New York: Garland Science (2011)).

Suitable methods of making antibodies are known in the art. For instance, standard hybridoma methods, EBV-hybridoma methods, bacteriophage vector expression systems, and methods of producing antibodies in non-human animals are described in, e.g., Murphy, supra.

Phage display also can be used to generate the antibody that may be used in the chimeric molecules of the invention. In this regard, phage libraries encoding antigen-binding variable (V) domains of antibodies can be generated using standard molecular biology and recombinant DNA techniques (see, e.g., Green et al. (eds.), *Molecular Cloning, A Laboratory Manual,* $4^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Murphy, supra).

Alternatively, antibodies can be produced by transgenic mice that are transgenic for specific heavy and light chain immunoglobulin genes. Such methods are known in the art and described in, for example, Murphy, supra.

Alternatively, the antibody can be a genetically-engineered antibody, e.g., a humanized antibody or a chimeric antibody. Humanized antibodies advantageously provide a lower risk of side effects and can remain in the circulation longer. Methods for generating humanized antibodies are known in the art and are described in detail in, for example, Murphy, supra). Humanized antibodies can also be generated using antibody resurfacing technology that is known in the art.

The targeting moiety may specifically bind to any suitable cell surface marker. The choice of a particular targeting moiety and/or cell surface marker may be chosen depending on the particular cell population to be targeted. Cell surface markers are known in the art (see, e.g., Mufson et al., *Front. Biosci.,* 11:337-43 (2006) and Kreitman et al., *AAPS Journal,* 8(3): E532-E551 (2006)) and may be, for example, a protein or a carbohydrate. In an embodiment of the invention, the targeting moiety is a ligand that specifically binds to a receptor on a cell surface. Exemplary ligands include, but are not limited to, vascular endothelial growth factor (VEGF), Fas, TNF-related apoptosis-inducing ligand (TRAIL), a cytokine (e.g., IL-2, IL-15, IL-4, IL-13), a lymphokine, a hormone, and a growth factor (e.g., transforming growth factor (TGFa), neuronal growth factor, epidermal growth factor).

The cell surface marker can be, for example, a cancer antigen. The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

Exemplary cancer antigens to which the targeting moiety may specifically bind include, but are not limited to mucin 1 (MUC1), melanoma associated antigen (MAGE), preferentially expressed antigen of melanoma (PRAME), carcinoembryonic antigen (CEA), prostate-specific antigen (PSA), prostate specific membrane antigen (PSMA), granulocyte-macrophage colony-stimulating factor receptor (GM-CSFR), CD56, human epidermal growth factor receptor 2 (HER2/neu) (also known as erbB-2), CD5, CD7, tyrosinase tumor antigen, tyrosinase related protein (TRP)1, TRP2, NY-ESO-1, telomerase, mesothelin, and p53. In a preferred embodiment, the cell surface marker, to which the targeting moiety specifically binds, is selected from the group consisting of cluster of differentiation (CD) 19, CD21, CD22, CD25, CD30, CD33, CD79b, B-cell maturation antigen (BCMA), glypican 2 (GPC2), glypican 3 (GPC3), transferrin receptor, EGF receptor (EGFR), mutated EGFR, mesothelin, cadherin, and Lewis Y. CD22 is expressed in, e.g., hairy cell leukemia, chronic lymphocytic leukemia (CLL), prolymphocytic leukemia (PLL), non-Hodgkin's lymphoma, small lymphocytic lymphoma (SLL), and acute lymphatic leukemia (ALL). CD25 is expressed in, e.g., leukemias and lymphomas, including hairy cell leukemia and Hodgkin's lymphoma. Lewis Y antigen is expressed in, e.g., bladder cancer, breast cancer, ovarian cancer, colorectal cancer, esophageal cancer, gastric cancer, lung cancer, and pancreatic cancer. CD33 is expressed in, e.g., acute myeloid leukemia (AML), chronic myelomonocytic leukemia (CML), and myeloproliferative disorders.

In an embodiment of the invention, the targeting moiety is an antibody that specifically binds to a cancer antigen. Exemplary antibodies that specifically bind to cancer antigens include, but are not limited to, antibodies against the transferrin receptor (e.g., HB21 and variants thereof), antibodies against CD22 (e.g., RFB4 and variants thereof), antibodies against CD25 (e.g., anti-Tac and variants thereof), antibodies against mesothelin (e.g., SS1, MORAb-009, SS, HN1, HN2, MN, MB, YP218, and variants thereof), antibodies against BCMA (BM24, BM306, and variants thereof), antibodies against GPC3 (YP7, HN3, and variants thereof), antibodies against GPC2 (LH1, LH4, LH7, and variants thereof), and antibodies against Lewis Y antigen (e.g., B3 and variants thereof). In this regard, the targeting moiety may be an antibody selected from the group consisting of B3, RFB4, SS, SS1, MN, MB, HN1, HN2, HB21, MORAb-009, YP218, YP7, HN3, LH1, LH4, LH7, BM24, BM306, and antigen binding portions thereof. Further exemplary targeting moieties suitable for use in the inventive chimeric molecules are disclosed e.g., in U.S. Pat. No. 5,242,824 (anti-transferrin receptor); U.S. Pat. No. 5,846,535 (anti-CD25); U.S. Pat. No. 5,889,157 (anti-Lewis Y); U.S. Pat. No. 5,981,726 (anti-Lewis Y); U.S. Pat. No. 5,990,296 (anti-Lewis Y); U.S. Pat. No. 7,081,518 (anti-mesothelin); U.S. Pat. No. 7,355,012 (anti-CD22 and anti-CD25); U.S. Pat. No. 7,368,110 (anti-mesothelin); U.S. Pat. No. 7,470,775 (anti-CD30); U.S. Pat. No. 7,521,054 (anti-CD25); and U.S. Pat. No. 7,541,034 (anti-CD22); U.S. Patent Application Publication 2007/0189962 (anti-CD22); Frankel et al., *Clin. Cancer Res.,* 6: 326-334 (2000), and Kreitman et al., *AAPS Journal,* 8(3): E532-E551 (2006), each of which is incorporated herein by reference. In another embodiment, the targeting moiety may include the targeting moiety of immunotoxins known in the art. Exemplary immunotoxins include, but are not limited to, LMB-2 (Anti-Tac(Fv)-PE38), BL22 and HA22 (RFB4(dsFv)-PE38), SS1P (SS 1 (dsFv)-PE38), HB21-PE40, and variants thereof. In a preferred embodiment, the targeting moiety is the antigen binding portion of HA22. HA22 comprises a disulfide-linked Fv anti-CD22 antibody fragment conjugated to PE38. HA22 and variants thereof are disclosed in International Patent Application Publications U.S. Pat. Nos. 8,809,502 and 8,871,906, which are incorporated herein by reference.

The inventive molecule may further comprise a second domain, which comprises an albumin binding domain (ABD). The ABD may be any moiety which specifically binds to serum albumin. The albumin, to which the ABD specifically binds, may be of any mammalian species. Preferably, the albumin is human serum albumin or mouse serum albumin.

In an embodiment of the invention, the ABD is a peptide which specifically binds to serum albumin. Any peptide which specifically binds to serum albumin may be suitable to include in the inventive chimeric molecules. The peptide may be from any species, e.g., *Streptococcus*. In an embodiment of the invention, the peptide, which specifically binds to serum albumin, is a streptococcal protein G-derived serum albumin binding domain. Such peptides are described, for example, in Jonsson et al., *Protein Engineering, Design & Selection,* 21(8): 515-27 (2008). In a preferred embodiment, the ABD is a peptide, which specifically binds to serum albumin, wherein the peptide comprises the amino acid sequence of SEQ ID NO: 2.

In an embodiment of the invention, the ABD is an antibody, or an antigen binding portion thereof, which specifically binds to serum albumin. Antibodies (and antigen binding portions thereof) which specifically bind to serum albumin may be as described herein for the targeting moiety with respect to other aspects of the invention with the exception that the antibodies (and antigen binding portions thereof) of the ABD specifically bind to serum albumin instead of the cell surface marker to which the antibodies (or antigen binding portions thereof) of the targeting moiety bind. In a preferred embodiment, the anti-albumin antibody is a single domain antibody. Antibodies which specifically bind to serum albumin are commercially available. The anti-albumin antibody may be of any species, e.g., llama. In a preferred embodiment, the antibody, or an antigen binding portion thereof, which specifically binds to serum albumin, is a single domain antibody from llama as described, for example, in Coppieters et al., *Arthritis & Rheumatism*, 54(6): 1856-66 (2006). In a preferred embodiment, the anti-albumin single domain antibody is ALB1 or MSA21, which are described in US 2007/0269422 and US 2006/0228355, respectively, each of which is incorporated herein by reference.

The inventive molecule may further comprise a third domain, which comprises a furin cleavage sequence ("FCS"), which FCS is cleavable by furin. The FCS may be a furin cleavage sequence of amino acid residues, which sequence is cleavable by furin and has an amino end and a carboxyl end. Without being bound by a particular theory or mechanism, it is believed that PEs containing the FCS undergo proteolytic processing inside target cells, thereby activating the cytotoxic activity of the toxin. The FCS of the inventive molecules may comprise any suitable furin cleavage sequence of amino acid residues, which sequence is cleavable by furin. Exemplary furin cleavage sequences are described in Duckert et al., *Protein Engineering, Design & Selection*, 17(1): 107-112 (2004) and U.S. Pat. No. 8,871,906, each of which is incorporated herein by reference. In an embodiment of the invention, FCS comprises residues 274-284 of SEQ ID NO: 1 (i.e., RHRQPRGWEQL (SEQ ID NO: 5)). Other suitable FCS amino acid sequences include, but are not limited to: R-X$_1$-X$_2$-R, wherein X$_1$ is any naturally occurring amino acid and X$_2$ is any naturally occurring amino acid (SEQ ID NO: 9), RKKR (SEQ ID NO: 10), RRRR (SEQ ID NO: 11), RKAR (SEQ ID NO: 12), SRVARS (SEQ ID NO: 13), TSSRKRRFW (SEQ ID NO: 14), ASRRKARSW (SEQ ID NO: 15), RRVKKRFW (SEQ ID NO: 16), RNVVRRDW (SEQ ID NO: 17), TRAVRRRSW (SEQ ID NO: 18), RQPR (SEQ ID NO: 19), RHRQPRGW (SEQ ID NO: 20), RHRQPRGWE (SEQ ID NO: 21), HRQPRGWEQ (SEQ ID NO: 22), RQPRGWE (SEQ ID NO: 23), RHRSKRGWEQL (SEQ ID NO: 24), RSKR (SEQ ID NO: 25), RHRSKRGW (SEQ ID NO: 26), HRSKRGWE (SEQ ID NO: 27), RSKRGWEQL (SEQ ID NO: 28), HRSKRGWEQL (SEQ ID NO: 29), RHRSKR (SEQ ID NO: 30), and R-X$_1$-X$_2$-R, wherein X$_1$ is any naturally occurring amino acid and X$_2$ is arginine or lysine (SEQ ID NO: 31).

In an embodiment of the invention, the FCS is represented by the formula P4-P3-P2-P1, wherein P4 is an amino acid residue at the amino end, P1 is an amino acid residue at the carboxyl end, P1 is an arginine or a lysine residue, and the sequence is cleavable at the carboxyl end of P1 by furin.

In another embodiment of the invention, the FCS (i) further comprises amino acid residues represented by P6-P5 at the amino end, (ii) further comprises amino acid residues represented by P1'-P2' at the carboxyl end, (iii) wherein if P1 is an arginine or a lysine residue, P2' is tryptophan, and P4 is arginine, valine or lysine, provided that if P4 is not arginine, then P6 and P2 are basic residues, and (iv) the sequence is cleavable at the carboxyl end of P1 by furin.

The inventive molecule may further comprise a fourth domain, which comprises an optionally substituted Domain III from *Pseudomonas* exotoxin A ("PE"). Domain III from PE is well known in the art, and numerous substitutions are known as well. Suitable substitutions in PE include those which remove one or more B-cell epitopes and/or one or more T-cell epitopes. Suitable substitutions of PE are known to those of ordinary skill in the art and some are set forth, for example, in U.S. Pat. Nos. 9,206,240 and 9,346,859, each of which is incorporated herein in its entirety by reference. In an embodiment of the invention, the inventive molecule optionally has (i) a further substitution of one or more amino acid residues within one or more T-cell epitopes, (ii) a further substitution of one or more amino acid residues within one or more B cell epitopes, (iii) a deletion of one or more contiguous amino acid residues of residues 1-273 and 285-394 as defined by SEQ ID NO: 1; or (iv) a combination of any of (i)-(iii), in the PE (e.g., Domain III of the PE). In an embodiment of the invention, the fourth domain comprises a PE amino acid sequence, wherein the PE amino acid sequence has a substitution of one or more of amino acid residues R427, F443, R456, D463, R467, L477, R490, R494, R505, R538, and L552, as defined by reference to SEQ ID NO: 1. In a preferred embodiment, the PE amino acid sequence has one or more of the following amino acid substitutions: R427A, F443A, R456A, D463A, R467A, L477H, R490A, R494A, R505A, R538A, and L552E, as defined by reference to SEQ ID NO: 1. See Mazor et al., *Molecular Cancer Therapy*, 2015, Dec., 14(12) 2789-96, which is incorporated herein in its entirety by reference.

The substitution of one or more amino acid residues within one or more T-cell epitopes may, advantageously, remove one or more T-cell epitopes and reduce T-cell immunogenicity as compared to a PE that lacks a substitution of one or more amino acid residues within one or more T-cell epitopes (e.g., wild-type PE). The substitution(s) may be located within any suitable PE T-cell epitope. Exemplary T-cell epitopes are disclosed in, for example, International Patent Application Publications WO 2012/170617, WO 2013/040141 and U.S. Pat. No. 9,206,240, each of which is incorporated herein by reference. In a preferred embodiment of the invention, the further substitution of one or more amino acid residues within one or more T-cell epitopes is a substitution of alanine, glycine, serine, or glutamine in place of one or more of amino acid residues L294, L297, Y298, L299, R302, R421, L422, L423, A425, L429, Y439, H440, F443, L444, A446, A447, I450, 464-466, 467, 468-480, 482-489, 490, 491-504, 505, 506-512, 513, 514-515, 517-519, L552, T554, I555, L556, and W558 of SEQ ID NO:1, wherein the amino acid residues L294, L297, Y298, L299, R302, R421, L422, L423, A425, L429, Y439, H440, F443, L444, A446, A447, I450, 464-466, 467, 468-480, 482-489, 490, 491-504, 505, 506-512, 513, 514-515, 517-519, L552, T554, I555, L556, and W558 are defined by reference to SEQ ID NO: 1. In an embodiment of the invention, the substitution of one or more amino acid residues at positions 464-466, 468-480, 482-489, 491-504, 506-512, 514-515, 517-519 may include, for example, a substitution of alanine, glycine, serine, or glutamine in place of one or more of amino acid residues at position 464, 465, 466, 468, 469, 470, 471, 472, 473, 474, 475, 476, 477, 478, 479, 480, 482, 483, 484, 485, 486, 487, 488, 489, 491, 492, 493, 494, 495, 496, 497, 498, 499, 500, 501, 502, 503, 504, 506, 507, 508, 509, 510, 511, 512, 514, 515, 517, 518, and 519, as defined by reference to SEQ ID NO: 1.

In an embodiment of the invention, any of the inventive molecules described herein has a further substitution of one or more amino acid residues within one or more B-cell epitopes. The substitution of one or more amino acid residues within one or more B-cell epitopes may, advantageously, remove one or more B-cell epitopes and reduce B-cell immunogenicity as compared to a PE that lacks a substitution of one or more amino acid residues within one or more B-cell epitopes (e.g., wild-type PE). The substitution(s) may be located within any suitable PE B-cell epitope. Exemplary B-cell epitopes are disclosed in, for example, International Patent Application Publications WO 2007/016150, WO 2009/032954, WO 2011/032022, WO 2012/170617, WO 2013/040141 and U.S. Pat. No. 9,206,240, each of which is incorporated herein by reference. In a preferred embodiment of the invention, the further substitution of one or more amino acid residues within one or more B-cell epitopes is a substitution of alanine, glycine, serine, or glutamine in place of one or more of amino acid residues E282, E285, P290, R313, N314, P319, D324, E327, E331, Q332, D403, D406, R412, R427, E431, R432, R456, R458, D461, D463, R467, Y481, R490, R505, R513, L516, E522, R538, E548, R551, R576, K590, Q592, and L597, wherein E282, E285, P290, R313, N314, P319, D324, E327, E331, Q332, D403, D406, R412, R427, E431, R432, R456, R458, D461, D463, R467, Y481, 8490, R505, 8513, L516, E522, R538, E548, R551, R576, K590, Q592, and L597 are defined by reference to SEQ ID NO: 1. In an embodiment of the invention, the amino acid residue at position 458 is arginine when amino acid residue R456 is substituted, preferably with alanine. Preferred mutations include those at positions R427, F443, R456, D463, R467, L477, R490, R494, R505, R538, and L552, including any combination of two or more (or all) of such.

In an embodiment of the invention, any of the inventive molecules described herein has a deletion of one or more contiguous amino acid residues of residues 1-273 and 285-394 as defined by SEQ ID NO: 1. The deletion of one or more contiguous amino acid residues of residues 1-273 and 285-394 may, advantageously, further reduce B- and/or T-cell immunogenicity.

In an embodiment of the invention, any of the inventive molecules described herein has a deletion of one or more contiguous amino acid residues of residues 253-273 and 285-394 as defined by SEQ ID NO: 1. The deletion of one or more contiguous amino acid residues of residues 253-273 and 285-394 may, advantageously, further reduce B- and/or T-cell immunogenicity.

The inventive molecule may be less immunogenic as compared to a molecule with PE that lacks (i) a further substitution of one or more amino acid residues within one or more T-cell epitopes, (ii) a further substitution of one or more amino acid residues within one or more B cell epitopes, (iii) a deletion of one or more contiguous amino acid residues of residues 1-273 and 285-394 as defined by SEQ ID NO: 1; or (iv) a combination of any of (i)-(iii), as described herein, if the immune response to the inventive molecule is diminished, quantitatively or qualitatively, as compared to the immune response to a molecule with a PE that lacks one or more of (i)-(iii). A quantitative decrease in immunogenicity encompasses a decrease in the magnitude or degree of the immune response. The magnitude or degree of immunogenicity can be measured on the basis of any number of known parameters, such as a decrease in the level of cytokine (e.g., antigen-specific cytokine) production (cytokine concentration), a decrease in the number of lymphocytes activated (e.g., proliferation of lymphocytes (e.g., antigen-specific lymphocytes)) or recruited, and/or a decrease in the production of antibodies (antigen-specific antibodies), etc. A qualitative decrease in immunogenicity encompasses any change in the nature of the immune response that renders the immune response less effective at mediating the reduction of the cytotoxic activity of the inventive molecule. Methods of measuring immunogenicity are known in the art. For example, measuring the types and levels of cytokines produced can measure immunogenicity. Alternatively or additionally, measuring the binding of PE to antibodies (e.g., antibodies previously exposed to PE) and/or measuring the ability of the PE to induce antibodies when administered to a mammal (e.g., humans, mice, and/or mice in which the mouse immune system is replaced with a human immune system) can measure immunogenicity. A less immunogenic PE may be characterized by a decrease in the production of cytokines such as any one or more of IFN-γ, TNF-α, and granzyme B, and/or a reduced stimulation of a cell-mediated immune response, such as a decrease in the proliferation and activation of T-cells and/or macrophages specific for PE as compared to that obtained with a PE that lacks one or more of (i)-(iii). Alternatively or additionally, less immunogenic PE may be characterized by an increase in the production of TGF-beta and/or IL-10 as compared to that obtained with a PE that lacks one or more of (i)-(iii). In an embodiment, reduced immunogenicity may be characterized by any one or more of a decrease in T cell stimulation, a decrease in T cell proliferation, and a decrease in T cell IFNγ and/or granzyme B secretion. Alternatively or additionally, a less immunogenic PE may be characterized by a decrease in the stimulation and/or activation of B-cells specific for PE as compared to that obtained with a PE that lacks one or more of (i)-(iii). For example, less immunogenic PE may be characterized by a decrease in the differentiation of B cells into antibody-secreting plasma cells and/or memory cells as compared to that obtained with a PE that lacks one or more of (i)-(iii). Reduced immunogenicity may be characterized by any one or more of a decrease in B cell stimulation, a decrease in B cell proliferation, and a decrease in anti-PE antibody secretion. Qualitative and quantitative diminishment of immunogenicity can occur simultaneously and are not mutually exclusive.

Any of the inventive molecules described herein may comprise PE with one or more further substitutions that may further increase cytotoxicity as disclosed, for example, in International Patent Application Publication WO 2007/016150, which is incorporated herein by reference. Increased cytotoxic activity and decreased immunogenicity can occur simultaneously, and are not mutually exclusive. Substitutions that both increase cytotoxic activity and decrease immunogenicity, such as substitutions of R490 to glycine or, more preferably, alanine, are especially preferred.

The inventive molecule may be configured in any of a variety of different ways. In an embodiment of the invention, the second domain is positioned between the first domain and the fourth domain. Alternatively or additionally, the third domain may be positioned between the first domain and the fourth domain. Alternatively or additionally, the second domain may be positioned between the first domain and the third domain. Alternatively or additionally, the third domain may be positioned between the second domain and the fourth domain. Alternatively or additionally, the first domain is positioned at the amino terminus of the molecule. Alternatively or additionally, the fourth domain is positioned at the carboxyl terminus of the molecule.

In an embodiment of the invention, the first domain is fused to the second domain directly or indirectly via a linker.

Alternatively or additionally, the second domain is fused to the third domain directly or indirectly via a linker. Alternatively or additionally, the third domain is fused to the fourth domain directly or indirectly via a linker. Alternatively or additionally, the first domain is positioned at the amino terminus of the molecule. Alternatively or additionally, the fourth domain is positioned at the carboxyl terminus of the molecule. Examples of molecules in accordance with embodiments of the invention are shown in FIGS. 2A-2D, 4B, 4D-4F, 12B-12C, 13B, and 13D.

In an embodiment of the invention, the inventive molecule comprises one or more linkers. In this regard, the inventive molecule may comprise (i) a linker positioned between the first domain and the second domain; (ii) a linker positioned between the second domain and the third domain; (iii) a linker positioned between the third domain and the fourth domain; (iv) a combination of any two of (i)-(iii); or (v) a combination of all three of (i)-(iii).

The term "linker" as used herein, refers to any agent or molecule that connects the various domains of the inventive molecule. In a preferred embodiment, the linker is a peptide linker. When the inventive molecule comprises more than one linker, the composition of each linker in the molecule may be the same or different. In an embodiment of the invention, any one or more of the linkers may, independently, consist of about one to about twenty amino acid residues selected, independently, from the group consisting of glycine, serine, lysine, and alanine. An example of such a linker may include, but is not limited to, KASGG (SEQ ID NO: 7). In a preferred embodiment of the invention, any one or more of the linkers independently consists of about one to about twenty amino acid residues selected, independently, from the group consisting of glycine and serine. In some embodiments, the linker is a peptide of the formula: (Xaa1)$_r$, wherein each Xaa1 is selected independently from glycine and serine and r is an integer from 1 to 20. Examples of such linkers include, but are not limited to: GGGGS (SEQ ID NO: 32), GGGGS GGGGS GGGGS (SEQ ID NO: 33), SGG (SEQ ID NO: 34), and GGGGS GGGGS GGGGS GG (SEQ ID NO: 35). In an especially preferred embodiment of the invention, the linker is GGS (SEQ ID NO: 8) or GSGSGSGSGSGSGSGSG (GS17) (SEQ ID NO: 37).

Another embodiment of the invention provides a molecule (e.g., chimeric molecule) comprising a sequence of Formula (I):

TM-R$^1_k$-ABD-R$^2_m$-FCS-R$^3_p$-R$^4_q$-PE functional domain III   (Formula I)

wherein:
TM is a targeting moiety;
R$^1$ is 1 to 20 amino acid residues;
k, m, p, and q are, independently, 0 or 1;
ABD is an albumin binding domain;
R$^2$ is 1 to 20 amino acid residues;
FCS is a furin cleavage sequence of amino acid residues, which sequence is cleavable by furin and has an amino end and a carboxyl end;
R$^3$ is 1 to 20 amino acid residues;
R$^4$ is 1 or more contiguous residues of residues 365-394 of SEQ ID NO: 1; and
PE functional domain III is residues 395-613 of Pseudomonas exotoxin A (PE) SEQ ID NO: 1, wherein the molecule has a deletion of amino acid residues 253-273 and 285-364 as defined by SEQ ID NO: 1.

The targeting moiety (TM) of Formula I may be as described herein with respect to other aspects of the invention.

R$^1$, R$^2$, and R$^3$ of Formula I may be, independently, any 1 to 20 amino acid residues, preferably any 5 to 15 amino acid residues. In an embodiment of the invention, R$^1$, R$^2$, and R$^3$ of Formula I are, independently, peptide linkers, which may be as described herein with respect to other aspects of the invention. In an embodiment of the invention, one or more of R$^1$, R$^2$, and R$^3$ of Formula I independently consist(s) of 1 to 20 amino acid residues selected, independently, from the group consisting of lysine, alanine, glycine, and serine. In a preferred embodiment, one or more of R$^1$, R$^2$, and R$^3$ of Formula I independently consist(s) of 1 to 20 amino acid residues selected, independently, from the group consisting of glycine and serine.

In Formula I, k, m, p, and q are, independently, 0 or 1. In an embodiment of the invention, k, m, and p are each 1 and q is 0.

In Formula I, ABD is an albumin binding domain. The ABD of Formula I may be as described herein with respect to other aspects of the invention.

In Formula I, FCS is a furin cleavage sequence of amino acid residues, which sequence is cleavable by furin and has an amino end and a carboxyl end. The FCS of Formula I may be as described herein with respect to other aspects of the invention.

In Formula I, R$^4$ is 1 or more contiguous residues of residues 365-394 of SEQ ID NO: 1.

In Formula I, PE functional domain III is residues 395-613 of Pseudomonas exotoxin A (PE) SEQ ID NO: 1. In an embodiment of the invention, the molecule of Formula I has a deletion of amino acid residues 253-273 and 285-364 as defined by SEQ ID NO: 1.

In an embodiment of the invention, the molecule of Formula I optionally has (i) a substitution of one or more amino acid residues within one or more T-cell epitopes, (ii) a substitution of one or more amino acid residues within one or more B cell epitopes, (iii) a deletion of one or more contiguous amino acid residues of residues 1-252 as defined by SEQ ID NO:1; or (iv) a combination of any of (i)-(iii) in the PE (e.g., functional domain III of the PE). The (i) substitution of one or more amino acid residues within one or more T-cell epitopes, (ii) substitution of one or more amino acid residues within one or more B cell epitopes, and (iii) deletion of one or more contiguous amino acid residues of residues 1-252 as defined by SEQ ID NO:1 may be as described herein with respect to other aspects of the invention.

In an embodiment of the invention, the molecule of Formula I has a substitution of one or more of amino acid residues R427, F443, R456, D463, R467, L477, R490, R494, R505, R538, and L552, as defined by reference to SEQ ID NO: 1, in PE functional domain III. In a preferred embodiment, the molecule of Formula I has one or more of the following amino acid substitutions: R427A, F443A, R456A, D463A, R467A, L477H, R490A, R494A, R505A, R538A, and L552E, as defined by reference to SEQ ID NO: 1, in PE functional domain III.

Included in the scope of the invention are functional portions of the inventive molecules described herein. The term "functional portion," when used in reference to a chimeric molecule, refers to any part or fragment of the chimeric molecule of the invention, which part or fragment retains the biological activity of the chimeric molecule of which it is a part (the parent chimeric molecule). Functional portions encompass, for example, those parts of a chimeric molecule that retain the ability to specifically bind to and destroy or inhibit the growth of target cells or treat or prevent cancer, to a similar extent, the same extent, or to a higher extent, as the parent chimeric molecule. In reference to the parent chimeric molecule, the functional portion can comprise, for instance, about 10% or more, about 25% or more, about 30% or more, about 50% or more, about 68% or more, about 80% or more, about 90% or more, or about 95% or more, of the parent chimeric molecule.

The functional portion can comprise additional amino acids at the amino or carboxyl terminus of the portion, or at both termini, which additional amino acids are not found in the amino acid sequence of the parent chimeric molecule. Desirably, the additional amino acids do not interfere with the biological function of the functional portion, e.g., specifically binding to and destroying or inhibiting the growth of target cells, having the ability to treat or prevent cancer, etc. More desirably, the additional amino acids enhance the biological activity, as compared to the biological activity of the parent chimeric molecule.

Included in the scope of the invention are functional variants of the inventive chimeric molecules described herein. The term "functional variant," as used herein, refers to a chimeric molecule having substantial or significant sequence identity or similarity to a parent chimeric molecule, which functional variant retains the biological activity of the chimeric molecule of which it is a variant. Functional variants encompass, for example, those variants of the chimeric molecule described herein (the parent chimeric molecule) that retain the ability to specifically bind to and destroy or inhibit the growth of target cells to a similar extent, the same extent, or to a higher extent, as the parent chimeric molecule. In reference to the parent chimeric molecule, the functional variant can, for instance, be about 30% or more, about 50% or more, about 75% or more, about 80% or more, about 90% or more, about 95% or more, about 96% or more, about 97% or more, about 98% or more, or about 99% or more identical in amino acid sequence to the parent chimeric molecule.

The functional variant can, for example, comprise the amino acid sequence of the parent chimeric molecule with at least one conservative amino acid substitution. Conservative amino acid substitutions are known in the art and include amino acid substitutions in which one amino acid having certain chemical and/or physical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent chimeric molecule with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent chimeric molecule.

The chimeric molecule of the invention can consist essentially of the specified amino acid sequence or sequences described herein, such that other components of the functional variant, e.g., other amino acids, do not materially change the biological activity of the functional variant.

The chimeric molecule of the invention (including functional portions and functional variants) of the invention can comprise synthetic amino acids in place of one or more naturally-occurring amino acids. Such synthetic amino acids are known in the art and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The chimeric molecule of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

An embodiment of the invention provides a method of producing the inventive molecule comprising (a) recombinantly expressing the molecule and (b) purifying the molecule. The chimeric molecules of the invention (including functional portions and functional variants) can be obtained by methods of producing proteins and polypeptides known in the art. Suitable methods of de novo synthesizing polypeptides and proteins are described in references, such as Dunn (ed.), *Peptide Chemistry and Drug Design*, 1st Ed., New York: Wiley (2015). Also, the chimeric molecules of the invention can be recombinantly expressed using the nucleic acids described herein using standard recombinant methods. See, for instance, Green et al., supra. In an embodiment of the invention, recombinantly expressing the inventive molecule comprises inserting a nucleotide sequence encoding a targeting moiety, a nucleotide sequence encoding an ABD, a nucleotide sequence encoding an FCS, a nucleotide sequence encoding a PE, and nucleotide sequence(s) encoding any linker(s) into a vector. The method may comprise inserting the nucleotide sequence encoding a targeting moiety, a nucleotide sequence encoding an ABD, a nucleotide sequence encoding an FCS, a nucleotide sequence encoding a PE, and nucleotide sequence(s) encoding any linker(s) in frame so that it encodes one continuous polypeptide including a functional targeting moiety domain, a functional ABD domain, a functional FCS domain, and a functional PE domain.

The method may further comprise purifying the inventive molecule. Once expressed, the inventive molecules may be purified in accordance with purification techniques known in the art. Exemplary purification techniques include, but are not limited to, ammonium sulfate precipitation, affinity columns, and column chromatography, or by procedures described in, e.g., Janson (ed.), *Protein Purification: Principles, High Resolution Methods, and Applications*, Springer-Verlag, NY (2011).

In another embodiment of the invention, the inventive molecules may be produced using non-recombinant methods. For example, the inventive molecules described herein (including functional portions and functional variants) can be commercially synthesized by companies, such as Synpep (Dublin, Calif.), Peptide Technologies Corp. (Gaithersburg, Md.), and Multiple Peptide Systems (San Diego, Calif.). In this respect, the inventive chimeric molecules can be synthetic, recombinant, isolated, and/or purified.

It may be desirable, in some circumstances, to free the PE from the targeting moiety and/or ABD when the chimeric molecule has reached one or more target cells. In this regard, the inventive chimeric molecules may comprise a cleavable linker. The linker may be cleavable by any suitable means, e.g., enzymatically. For example, when the target cell is a cancer (e.g., tumor) cell, the chimeric molecule may include a linker cleavable under conditions present at the tumor site (e.g. when exposed to tumor-associated enzymes or acidic pH).

An embodiment of the invention provides a nucleic acid comprising a nucleotide sequence encoding any of the inventive chimeric molecules described herein. The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated and/or purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Co.) and Synthegen (Houston, Tex.).

An embodiment of the invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive chimeric molecules. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). Preferably, the recombinant expression vector is a viral vector, e.g., a retroviral vector.

The recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive chimeric molecule (including functional portions and functional variants), or to the nucleotide sequence which is complementary to or which hybridizes to the nucleotide sequence encoding the chimeric molecule. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to a cell that can contain the inventive recombinant expression vector. For purposes of producing a recombinant inventive chimeric molecule, the host cell is preferably a prokaryotic cell (e.g., a bacteria cell), e.g., an E. coli cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive chimeric molecules (including functional portions and functional variants), nucleic acids, recombinant expression vectors, host cells (including populations thereof), and populations of cells can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive chimeric molecules (including functional portions and functional variants), nucleic acids, recombinant expression vectors, host cells (including populations thereof), and populations of cells, all of which are collectively referred to as "inventive PE materials" hereinafter, can be formulated into a composition, such as a pharmaceutical composition. In this regard, the invention provides a pharmaceutical composition comprising any of the chimeric molecules (including functional portions and functional variants), nucleic acids, recombinant expression vectors, host cells (including populations thereof), or populations of cells, and a pharmaceutically acceptable carrier. The inventive pharmaceutical composition containing any of the inventive PE materials can comprise more than one inventive PE material, e.g., a polypeptide and a nucleic acid, or two or more different PEs. Alternatively, the pharmaceutical composition can comprise an inventive PE material in combination with one or more other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound (s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive PE material, as well as by the particular method used to administer the inventive PE material. Accordingly, there are a variety of suitable formulations of the pharmaceutical composition of the invention. The following formulations for parenteral (e.g., subcutaneous, intravenous, intraarterial, intramuscular, intradermal, interperitoneal, and intrathecal) administration are exemplary and are in no way limiting. More than one route can be used to administer the inventive PE materials, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive PE material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive PE material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art (see, e.g., Lloyd et al. (eds.), *Remington: The Science and Practice of Pharmacy,* 22nd Ed., Pharmaceutical Press (2012)).

It will be appreciated by one of skill in the art that, in addition to the above-described pharmaceutical compositions, the inventive PE materials of the invention can be formulated as inclusion complexes, such as cyclodextrin inclusion complexes, or liposomes.

For purposes of the invention, the amount or dose of the inventive PE material administered should be sufficient to effect a desired response, e.g., a therapeutic or prophylactic response, in the mammal over a reasonable time frame. For example, the dose of the inventive PE material should be sufficient to inhibit growth of a target cell or treat or prevent cancer in a period of from about 2 hours or longer, e.g., 12 to 24 or more hours, from the time of administration. In certain embodiments, the time period could be even longer. The dose will be determined by the efficacy of the particular inventive PE material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of symptoms), $LD_{50}$ (the dose lethal to 50% of the population), the $ED_{50}$ (the dose therapeutically effective in 50% of the population), and the therapeutic index in cell culture and/or animal studies. The therapeutic index is the ratio of $LD_{50}$ to $ED_{50}$ (i.e., $LD_{50}/ED_{50}$).

The dose of the inventive PE material also will be determined by the existence, nature, and extent of any adverse side effects that might accompany the administration of a particular inventive PE material. Typically, the attending physician will decide the dosage of the inventive PE material with which to treat each individual patient, taking into consideration a variety of factors, such as age, body weight, general health, diet, sex, inventive PE material to be administered, route of administration, and the severity of the condition being treated. By way of example and not intending to limit the invention, the dose of the inventive PE material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, or about 10 mg/kg body weight/day.

The inventive PE materials may be assayed for cytotoxicity by assays known in the art. Examples of cytotoxicity assays include a WST assay, which measures cell proliferation using the tetrazolium salt WST-1 (reagents and kits available from Roche Applied Sciences), as described in International Patent Application Publication WO 2011/032022.

It is contemplated that the inventive chimeric molecules, nucleic acids, recombinant expression vectors, host cell, population of cells, and pharmaceutical compositions can be used in methods of treating or preventing cancer. Without being bound by a particular theory or mechanism, it is believed that the inventive chimeric molecules destroy or inhibit the growth of cells. Without being bound to a particular theory or mechanism, it is believed that the inventive chimeric molecules recognize and specifically bind to cell surface markers, thereby delivering the cytotoxic PE to the population of cells expressing the cell surface marker with minimal or no cross-reactivity with cells that do not express the cell surface marker. In this way, the cytotoxicity of PE can be targeted to destroy or inhibit the growth of a particular population of cells, e.g., cancer cells. In this regard, an embodiment of the invention provides a method of treating or preventing cancer in a mammal comprising administering to the mammal any of the inventive chimeric molecules, nucleic acids, recombinant expression vectors, host cell, population of cells, or pharmaceutical compositions described herein, in an amount effective to treat or prevent cancer in the mammal.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

With respect to the inventive methods, the cancer can be any cancer, including any of adrenal gland cancer, sarcomas (e.g., synovial sarcoma, osteogenic sarcoma, leiomyosarcoma uteri, angiosarcoma, fibrosarcoma, rhabdomyosarcoma, liposarcoma, myxoma, rhabdomyoma, fibroma, lipoma, and teratoma), lymphomas (e.g., small lymphocytic lymphoma, Hodgkin lymphoma, and non-Hodgkin lymphoma), hepatocellular carcinoma, glioma, head cancers (e.g., squamous cell carcinoma), neck cancers (e.g., squamous cell carcinoma, acute lymphocytic cancer, leukemias (e.g., hairy cell leukemia, myeloid leukemia (acute and chronic), lymphatic leukemia (acute and chronic), prolymphocytic leukemia (PLL), myelomonocytic leukemia (acute and chronic), and lymphocytic leukemia (acute and chronic)), bone cancer (osteogenic sarcoma, fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors), brain cancer (astrocytoma, medulloblastoma, glioma, ependymoma, germinoma (pinealoma), glioblastoma multiforme, oligodendroglioma, schwannoma, and retinoblastoma), fallopian tube cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva (e.g., squamous cell carcinoma, intraepithelial carcinoma, adenocarcinoma, and fibrosarcoma), myeloproliferative disorders (e.g., chronic myeloid cancer), colon cancers (e.g., colon carcinoma), esophageal cancer (e.g., squamous cell carcinoma, adenocarcinoma, leiomyosarcoma, and lymphoma), cervical cancer (cervical carcinoma and pre-invasive cervical dysplasia), gastric cancer, gastrointestinal carcinoid tumor, hypopharynx cancer, larynx cancer, liver cancers (e.g., hepatocellular carcinoma, cholangiocarcinoma, hepatoblastoma, angiosarcoma, hepatocellular adenoma, and hemangioma), lung cancers (e.g., bronchogenic carcinoma (squamous cell, undifferentiated small cell, undifferentiated large cell, and adenocarcinoma), alveolar (bronchiolar) carcinoma, bronchial adenoma, chondromatous hamartoma, small cell lung cancer, non-small cell lung cancer, and lung adenocarcinoma), malignant mesothelioma, skin cancer (e.g., melanoma, basal cell carcinoma, squamous cell carcinoma, Kaposi's sarcoma, nevi, dysplastic nevi, lipoma, angioma, dermatofibroma, and keloids), multiple myeloma, nasopharynx cancer, ovarian cancer (e.g., ovarian carcinoma (serous cystadenocarcinoma, mucinous cystadenocarcinoma, endometrioid carcinoma, and clear cell adenocarcinoma), granulosa-theca cell tumors, Sertoli-Leydig cell tumors, dysgerminoma, and malignant teratoma), pancreatic cancer (e.g., ductal adenocarcinoma, insulinoma, glucagonoma, gastrinoma, carcinoid tumors, and VIPoma), peritoneum, omentum, mesentery cancer, pharynx cancer, prostate cancer (e.g., adenocarcinoma and sarcoma), rectal cancer, kidney cancer (e.g., adenocarcinoma, Wilms tumor (nephroblastoma), and renal cell carcinoma), small intestine cancer (adenocarcinoma, lymphoma, carcinoid tumors, Kaposi's sarcoma, leiomyoma, hemangioma, lipoma, neurofibroma, and fibroma), soft tissue cancer, stomach cancer (e.g., carcinoma, lymphoma, and leiomyosarcoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), cancer of the uterus (e.g., endometrial carcinoma), thyroid cancer, and urothelial cancers (e.g., squamous cell carcinoma, transitional cell carcinoma, adenocarcinoma, ureter cancer, and urinary bladder cancer). In a preferred embodiment, the cancer is a cancer that is characterized by the expression or overexpression of CD22 (such as, for example, hairy cell leukemia, CLL, PLL, non-Hodgkin's lymphoma, SLL, and ALL), BCMA (such as, for example, multiple myeloma and Hodgkin's lymphoma), or mesothelin (such as, for example, mesothelioma and ovarian and pancreatic adenocarcinoma).

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Also provided is a method of inhibiting the growth of a target cell comprising contacting the cell with any of the inventive chimeric molecules, nucleic acids, recombinant expression vectors, host cell, population of cells, or pharmaceutical compositions described herein, in an amount effective to inhibit growth of the target cell. The growth of the target cell may be inhibited by any amount, e.g., by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%. The target cell may be provided in a biological sample. A biological sample may be obtained from a mammal in any suitable manner and from any suitable source. The biological sample may, for example, be obtained by a blood draw, leukapheresis, and/or tumor biopsy or necropsy. The contacting step can take place in vitro or in vivo with respect to the mammal. Preferably, the contacting is in vitro.

In an embodiment of the invention, the target cell is a cancer cell. The target cell may be a cancer cell of any of the cancers described herein. In an embodiment of the invention, the target may express a cell surface marker. The cell surface marker may be any cell surface marker described herein with respect to other aspects of the invention. The cell surface marker may be, for example, selected from the group consisting of CD19, CD21, CD22, CD25, CD30, CD33, CD79b, transferrin receptor, EGF receptor (EGFR), mutated EGFR, BCMA, glypican 2 (GPC2), glypican 3 (GPC3), mesothelin, cadherin, and Lewis Y.

The following examples further illustrate the invention but, of course, should not be construed as in any way limiting its scope.

EXAMPLES

A 54 amino acid albumin binding peptide from *Streptococcus* (Jonsson et al., *Protein Eng. Des. Sel.* 21(8); 515-527 (2008) and WO 2005/097202) (SEQ ID NO: 2) referred to as ABD-S, was used in the following examples. Two single domain antibodies from Llama (ALB1 and MSA21) that also bind to albumin and increase half-life (Coppieters et al., *Arthritis & Rheumatology* 54 (6); 1856-1866 (2006)) were also used in the following examples. ALB1 and MSA21 are described in US 2007/0269422 and US 2006/0228355, respectively.

Example 1

This example demonstrates the preparation of RITs containing ABDs.

To prepare RITs that bind to albumin, each of the albumin binding moieties were inserted after the Fv and before the furin cleavage site (FCS) as shown in FIGS. 2A-2D. For purposes of comparison, immunotoxins lacking ABDs were also prepared as shown in FIGS. 1A-1D.

Comparative Example 1

This comparative example illustrates the challenges to successfully producing an immunotoxin with a useful increase in cell killing or anti-tumor activity.

The approach of inserting extra Fv domains close to or next to the amino terminal Fv was previously tried with immunotoxins containing PE38 and PE24 and for unknown reasons was not successful. Either the proteins could not be made, presumably due to refolding issues, or only small amounts could be made. Even with those that could be made in small amounts, there was no useful increase in cell killing or anti-tumor activity, as described below.

The RIT constructs shown in FIGS. 3A-3C and 3F-3G did not produce any pure protein due to mis-folding and aggregation. In the case of e23-bdsFv-PE38 (3D), only 0.8 mg of pure protein was produced, starting with 100 mg of inclusion bodies (Bera et al., *J Bioconjugate Chem.* 9(6), 736-743 (1998)). Poor yield limited testing of the activity and the properties of the protein. In the case of SS1-bdsFv-PE38 (3E), protein was produced with reasonable yield, but its activity was not increased in an animal model (Bera et al., *Mol. Cancer Ther.* 1:79-84 (2001)).

Example 2

This example demonstrates that inserting ABDs after the Fv and before the FCS provides high yields of purified proteins.

The immunotoxin constructs shown in FIGS. 4A-4F were prepared. The purity and yields of protein obtained with the ABD containing immunotoxin constructs shown FIGS. 4A-4F is summarized in Table 1, below. Inserting the ABDs after the Fv and before the 11-amino acid FCS surprisingly produced large amounts of very pure protein (FIG. 5, SDS gels) with high yields, based on the amount of starting protein. In the cases of LMB-164 (4B) and LMB-182 (4D), yields of 24% and 38%, respectively, of highly purified protein were obtained. Such yields are needed for the successful production of material for clinical use.

TABLE 1

Protein yields

| LMB number | Descriptive Name | Inclusion body for making protein (mg) | Yield of the protein (mg) |
|---|---|---|---|
| LMB-164 | SS1-ABD-dsFv-LRGGS | 100 | 24 |
| LMB-182 | SS1-ABD-dsFv-T20 | 100 | 38 |
| LMB-170 | SS1-ALB1-LRGGS | 100 | 3.7 |
| LMB-172 | SS1-MSA21-LRGGS | 100 | 10 |

Example 3

This example demonstrates that RIT constructs containing the ABD-S insert have cytotoxic activity.

Cytotoxicity assays of the albumin binding constructs were performed on four cancer cell lines (A431/H9, L55, MKN74, and KLM1) by WST-8 cell proliferation assay for 72 hours, as shown in FIGS. 6A-6D. The cytotoxicity assays revealed that LMB-164 (the RIT containing the 54-amino acid peptide ABD-S) is very active on all 4 lines with $IC_{50}$s close to the $IC_{50}$s of the parent LMB-12. LMB-182 is about 2-fold less active than its parent LMB-20. LMB-172 had similar activities to LMB-164. LMB-170 was about 2-fold less active that LMB-172 but still very active killing cells in the low ng/ml range. In summary, all ABD containing RITs had good cytotoxic activity but the RIT with the 54-amino acid peptide was the best. The results of the cytotoxicity assays are provided below in Table 2.

TABLE 2

Summary of IC$_{50}$ assays on cancer cell lines
(averages from 2-4 experiments)

|  | Cell line | LMB-12 | LMB-164 | LMB-20 | LMB-182 | LMB-170 | LMB-172 |
|---|---|---|---|---|---|---|---|
| IC$_{50}$ (ng/ml) | KLM1 | 0.71 | 0.77 | 1.06 | 1.8 | 1.7 | 0.6 |
|  | A431/H9 | 0.23 | 0.24 | 0.17 | 0.54 | 0.26 | 0.13 |
|  | L-55 | 1.96 | 2.8 | 1.8 | 3.5 | 5.8 | 2.2 |
|  | MKN-28 | 0.2 | 0.2 | 0.27 | 0.54 | 0.63 | 0.18 |

Example 4

This example demonstrates that RIT constructs LMB-164, LMB-170, and LMB-172 bind to human serum albumin (HSA).

To determine if LMB-12, LMB-164, LMB-170 and LMB-172 could bind to MSA, HSA, and BSA, albumin binding experiments were carried out in an ELISA format. Three plates were coated with MSA, HSA, and BSA respectively, with 2 ug/ml, at 50 ul/well at 4° C. overnight. Serially diluted immunotoxins were added by casein blocking buffer (0.5 ug/ml to 0.225 ng/ml, 3-fold dilution), at room temperature for 2 hours. Then IP12 I ug/ml, 50 ul/well was added at room temperature for 1 hour. Anti-mouse IgG-HRP was then added at room temperature for 1 hour. The TMB substrate (3,3',5,5'-Tetramethylbenzidine) was then added. As shown in FIGS. 7A-7C, LMB-12 did not bind to any of the albumins as expected, because it has no ABD insert. While LMB-164, LMB-170 and LMB-172 can bind to MSA, the binding capacity of LMB-164 is about 5-fold and 23-fold of those of LMB-172 and LMB-170, respectively. LMB-12 cannot bind MSA. LMB-164, LMB-170 and LMB-172 all show similar binding capacity to HSA. None of these proteins bound BSA (7C). The results of the albumin binding experiments on MSA and HSA are shown below in Table 3. The albumin binding experiments on BSA did not produce any results.

TABLE 3

Summary of affinity to albumin of all ABD immunotoxins and native immunotoxins

| LMB Number | Name of Protein | MSA Affinity nM (n = 3) | HSA Affinity nM (n = 3) |
|---|---|---|---|
| LMB-12 | SS1-LR-GGS (PE24) | none | none |
| LMB-164 | SS1-ABD-dsFv-LRGGS-PE24 | 0.10 | 0.08 |
| LMB-20 | SS1-dsFv-T20 | no binding | no binding |
| LMB-182 | SS1-ABD-dsFv-T20 | 0.11 | 0.09 |
| LMB-170 | SS1-ALB1-dsFv-LRGGS | 2.15 | 0.12 |
| LMB-172 | SS1-MSA21-dsFv-LRGGS | 0.4 | 0.09 |
| LMB-209 | SS1-ABD-dsFv-PE38 | 0.16 | 0.11 |

Example 5

This example demonstrates that inserting an ABD into an RIT construct significantly increases half-life.

As shown in FIGS. 8A-8F, LMB-12, LMB-20, LMB-164, LMB-182, LMB-172, and LMB-170 were injected into mice, blood was collected at various time points, and blood levels were measured by an ELISA method. The half-lives (the time required for a 50% decrease in blood levels) of the new immunotoxin constructs were calculated, as provided in Table 4. An immunotoxin in which domain III has mutations that remove human T cell epitopes (LMB-182) was made and its half-life was measured. LMB-20, the same protein with no ABD insert, was also made and its half-life was measured. The half-life was increased from 7 minutes for LMB-20 to 130 minutes for LMB-182. The data shown in FIGS. 8A-8F and summarized in Table 4, show that all of the new immunotoxin constructs had extended half-lives. For example, the half-life of LMB-164 is 150 minutes, compared to just 18 minutes for LMB-12 which has no ABD insert.

TABLE 4

RIT half-life results-Averages
Average of 4 mice in each group

| Protein | Half life (mins) | AUC |
|---|---|---|
| LMB-12 | 13 | 298 |
| LMB-20 | 8 | 242 |
| LMB-164 | 185 | 10373 |
| LMB-182 | 143 | 8073 |
| LMB-172 | 143 | 9345 |
| LMB-170 | 97 | 4378 |

Example 6

This example demonstrates that the RIT constructs containing the ABD-S sequence show anti-tumor activity in a human pancreatic cancer cell line.

The anti-tumor activity of the immunotoxin constructs LMB-164 and LMB-12 were tested in mice bearing KLM-1, a human pancreatic cancer cell line. Control mice were injected with phosphate buffered saline (PBS), which is the diluent. The graphs in FIGS. 9 and 10 show the results of mice treated intravenously with 6 ug per day of either LMB-164 or its parent LMB-12. In both of FIGS. 9 and 10, LMB-164 was provided by IV at a dosage of 6 µg/mouse on days 5-9 and days 12-15 and LMB-12 was provided by IV at a dosage of 6 µg/mouse on days 5-9 and days 12-15. The data in FIG. 9 shows that LMB-164 is more effective than LMB-12 in reducing tumor volume. LMB-164 produced tumor regressions in all mice with complete disappearance of tumors in 6/8 mice, whereas LMB-12 slowed growth but did not produce any tumor regressions. The mice treated with either LMB-164 or LMB-12 were healthy during the experiment with no animals dying or losing over 5% of body weight, as shown in FIG. 10.

The anti-tumor activities of LMB-182 were also compared with that of LMB-164 (FIG. 11). LMB-182 contains a PE domain III with mutations that remove human T cell epitopes, and is about 2-fold less active than LMB-12 so higher doses were given to the mice. LMB-164 was provided by IV at a dosage of 6 µg/mouse on days 5-10 and days 13-15. LMB-164 was provided by IV at a dosage of 10

μg/mouse on days 5-8 and days 13-15. LMB-182 was provided by IV at a dosage of 6 μg/mouse on days 5-10 and days 13-15. LMB-182 was provided by IV at a dosage of 10 μg/mouse on days 5-10 and days 13-15. LMB-182 was provided by IV at a dosage of 20 μg/mouse on days 5-10 and days 13-15. LMB-164 at a dosage of 6 μg and 10 μg injected daily produced striking tumor regressions. LMB-184 provided at dosages of 6 μg, 10 μg, or 20 ug were very effective but not as active as LMB-164.

The anti-tumor activity of various PE immunotoxin constructs is summarized below in Table 5.

TABLE 5

Summary of anti-tumor activity

| LMB-164 | A mixture of complete responses and almost complete responses when 10 ug given for 6 daily doses |
| --- | --- |
| LMB-170 | Stable disease (SD) at 10 μg and 20 μg or 30 ug |
| LMB-172 | Stable disease at 10 ug 4 times, 20 ug 3 times or 30 ug one time, More was toxic to mice. |
| LMB-167 | Partial response (PR) at 3 μg |
| M1-PE38-ABD | Partial response (PR) at 3 μg |

The anti-tumor activities of RITs with ABDs from Llama were also examined. LMB-170 was tested at 10 μg, 20 μg, or 30 μs per dose. Mice treated with 30 μg lost weight and were not valuable for response. Mice treated with 10 μg or 20 μg showed tumor stabilization but no striking regressions were observed. Similar responses were observed in mice treated with LMB-172. In summary, the tumors were less responsive to the immunotoxin constructs with Llama single domain antibodies than with the ABD from *Streptococcus*.

Example 7

This example demonstrates that RITs having ABD-S placed in regions other than after the Fv and before the furin peptide are less effective.

To determine if the ABD-S from *Streptococcus* could be placed at other regions in a RIT, an immunotoxin (anti-Tac-M1-PE38) targeting CD25 (Onda et al., J Immunol. 163; 6072-6077 (1999)) was used (FIG. 12A). The protein has the same design as SS1P, but recognizes CD25 instead of mesothelin. The 54-amino acid ABD-S was inserted near the end of domain III, but before the REDLK sequence (SEQ ID NO:36) needed to translocate the immunotoxin to the endoplasmic reticulum (FIG. 12C). The results are shown in Table 6. The protein Ml-PE38-ABD-S had a 6-fold decrease in cytotoxic activity on cell line ATAC4 and a more than 25-fold decrease in activity on Karpas cells, as compared to aTac-M1-PE38. An RIT construct where the ABD is placed at the amino terminus of the Fv was prepared (LMB-167), as shown in FIG. 12B. LMB-167 has a 3-fold decrease in cytotoxic activity on ATAC4 cell line and a 10-fold decrease in activity on Karpass 299 cell line as compared to aTac-M1-PE38.

TABLE 6

In vitro activity of immunotoxins on Atac4 and Karpas 299 cells

| Immunotoxin | $IC_{50}$ on Atac4 cells (ng/ml) | $IC_{50}$ on Karpas 299 cells (ng/ml) |
| --- | --- | --- |
| aTac-M1-PE38 | 0.026 | 0.19 |
| LMB 167 | 0.08 | 1.9 |
| M1-PE38-ABD | 0.17 | 4.9 |

Example 8

This example demonstrates that the RIT containing an ABD design can be used to make immunotoxins targeting additional cancer antigens. ABD-S containing immunotoxins with Fvs targeted at CD22 on leukemia cells (LMB-196, FIG. 13D) and BCMA on myeloma cells (LMB-162, FIG. 13B) were prepared. The resulting data provided below in Table 7 indicates that this approach can be used to make immunotoxins targeting other cancer antigens. The production yields are very good and the proteins have high cytotoxic activity.

TABLE 7

Yields and $IC_{50}$ targets of BM306 and HA22 ABD constructs.

| Immunotoxin | Yield | $IC_{50}$ in target cells |
| --- | --- | --- |
| LMB-75 anti-BCMA | 20% | 1.3 ng/ml |
| LMB-162 anti-BCMA | 25% | 1.4 ng/ml |
| LMB-13 Anti-CD22 | 10% | 0.2 ng/ml |
| LMB-196 Anti-CD22 | 14% | 0.3 ng/ml |

Example 9

This example demonstrates that RITs in which an ABD is inserted and include a mutant form of PE38 have low cell toxicity.

To confirm the lower cytotoxic activity of a protein in which an ABD is included in an RIT with a mutant form of PE38, an RIT with PE38 that targets mesothelin (LMB-209) was made and tested on KLM-1 cells, as follows: LMB-12, LMB-164, and LMB-209 were assayed on KLM1 cell lines by WST-8 for 72 hours. First, KLM1 cells were plated in 96 well plate 4000 cells/well and the immunotoxins were diluted with 1:3 ratio from 300 ng/ml. After 3 days, 20 μl of 1:1 diluted WST (PBS dilution) was added, then incubated at 37° C. 5% $CO_2$ for 2-3 hr until the medium color turned to yellow. The immunotoxin was found to be 6-fold less active than LMB-164 (which has no domain II) on KLM-1 cells (FIG. 14).

Example 10

This example demonstrates that the serum half-life of ABD-containing RITs are significantly higher than immunotoxin constructs which do not contain ABDs.

Recombinant immunotoxins with Fvs targeted at BCMA on myeloma cells were constructed (Table 8), using LMB-75 as the parent immunotoxin (FIG. 13A). To increase the serum half-life in vivo, the RITs were fused with either a 54 amino acid albumin binding domain from *Streptococcus*

(SEQ ID NO: 2) (ABD-S), as exemplified by LMB-162 (FIG. 13B), or a 115 amino acid single domain antibody MSA21 from llama.

The constructed RITs are listed below in Table 8. LMB-173 (FIG. 17A) was constructed similarly to LMB-162, but includes the 115 amino acid single domain antibody MSA21 instead of ABD-S from *Streptococcus*. LMB-224 (in bold) (FIG. 17B) was constructed similarly to LMB-162, but the ABD (ABD-S) is flanked on both sides with 9 amino acid GS9 peptide linkers (SEQ ID NO: 38). LMB-235 (FIG. 17C) was constructed with the 54 amino acid ABD-S albumin binding domain attached to the BCMA targeting moiety at the amino terminus of the heavy chain variable region. LMB-237 (FIG. 17D) was constructed with the 54 amino acid ABD-S albumin binding domain attached to the BCMA targeting moiety at the amino terminus of the light chain variable region.

The in vitro activity of these immunotoxins is summarized in Table 8. As shown, the serum half-life of ABD-fusion protein is significantly higher (148 minutes) than the parent immunotoxin LMB-75 (7.4 minutes). However, all ABD-fusion proteins are little less active in vitro compared to the parent immunotoxin LMB-75.

TABLE 8

IC$_{50}$ and half-life of recombinant immunotoxins targeting BCMA-expressing multiple myeloma cells

| RIT | Description | IC$_{50}$ (ng/ml) | Half-life (Minutes) |
|---|---|---|---|
| LMB-75 | BM306-dsFv-LRggs | 0.9 | 7.4 |
| LMB-162 | BM306-dsFv-ABD-S-LRggs | 3.6 | 148 |
| LMB-173 | BM306-dsFv-MSA21-LRggs | 2.4 | Not yet determined |
| LMB-224 | BM306-dsFv-GS9-ABD-S-GS9-LRggs | 2.9 | Not yet determined |
| LMB-235 | BM306-ABD-S-GS17-VH-dsFv-LRggs | 3.0 | Not yet determined |
| LMB-237 | BM306-ABD-S-GS17-VL-dsFv-LRggs | 3.6 | Not yet determined |

Example 11

This example demonstrates that the ABD-containing immunotoxin LMB-224 is active in vivo.

To investigate the in vivo activity of immunotoxins with the ABD-S albumin binding domain fusion protein, a H929 GFP-Luciferase myeloma mouse model was established. The activity of one of the anti-BCMA-ABD immunotoxins, LMB-224 (Table 8, bold; FIG. 17B) was tested. Immunodeficient NSG mice were intravenously injected with 1E7 H929-luc-GFP cells for bioluminescence imaging (FIGS. 15A-C). Mice were treated beginning on day 4 with either PBS (control) or 0.5 and 0.25 mg/kg every other day for a total of 5 doses of LMB-224. The tumor burden was assessed with bioluminescence imaging on days 4, 11, and 17. As shown in FIGS. 15A-15C, LMB-224 is very active in vivo. Both LMB-224 treatment groups resulted in complete recovery of all treated mice (Day 11, FIG. 15B and day 17, FIG. 15C) with no significant weight loss due to treatment associated toxicity (FIGS. 16A-C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A molecule comprising:
   (a) a first domain, which comprises a targeting moiety, wherein the targeting moiety is not an affibody;
   (b) a second domain, which comprises an albumin binding domain (ABD) and comprises the amino acid sequence of SEQ ID NO: 2,
   (c) a third domain, which comprises a furin cleavage sequence (FCS) which FCS is cleavable by furin; and
   (d) a fourth domain, which comprises a Domain III from *Pseudomonas* exotoxin A (PE) or a Domain III from *Pseudomonas* exotoxin A (PE) comprising a substitution of one or more amino acid residues;

wherein the second domain is positioned between the first domain and the third domain;

wherein the third domain is positioned between the second domain and the fourth domain; and wherein the molecule optionally has (i) a substitution of one or more amino acid residues within one or more T-cell epitopes, (ii) a substitution of one or more amino acid residues within one or more B cell epitopes, (iii) a deletion of one or more contiguous amino acid residues of residues 1-273 and 285-394 as defined by SEQ ID NO:1; or (iv) a combination of any of (i)-(iii).

2. The molecule of claim 1, further comprising:
(i) a linker positioned between the first domain and the second domain;
(ii) a linker positioned between the second domain and the third domain;
(iii) a linker positioned between the third domain and the fourth domain;

(iv) a combination of any two of (i)-(iii); or (v) a combination of all three of (i)-(iii).

3. The molecule of claim 2, wherein the linker of any one or more of (i)-(iii) consist(s) of 1 to 20 amino acid residues selected, independently, from the group consisting of glycine, serine, lysine, and alanine.

4. The molecule of claim 2, wherein the linker of any one or more of (i)-(iii) consist(s) of 1 to 20 amino acid residues selected, independently, from the group consisting of glycine and serine.

5. The molecule of claim 1, wherein the fourth domain comprises a PE amino acid sequence, wherein the PE amino acid sequence has a substitution of one or more of amino acid residues R427, F443, R456, D463, R467, L477, R490, R494, R505, R538, and L552, as defined by reference to SEQ ID NO: 1.

6. The molecule of claim 1, wherein the fourth domain comprises a PE amino acid sequence, wherein the PE amino acid sequence has one or more of the following amino acid substitutions: R427A, F443A, R456A, D463A, R467A, L477H, R490A, R494A, R505A, R538A, and L552E, as defined by reference to SEQ ID NO: 1.

7. A molecule comprising a sequence of Formula (I):

$$TM\text{-}R^1_k\text{-}ABD\text{-}R^2_m\text{-}FCS\text{-}R^3_p\text{-}R^4_q\text{-}PE \text{ functional domain III} \quad \text{(Formula I)}$$

wherein:
TM is a targeting moiety;
$R^1$ is 1 to 20 amino acid residues;
k, m, p, and q are, independently, 0 or 1;
ABD is an albumin binding domain and comprises the amino acid sequence of SEQ ID NO: 2;
$R^2$ is 1 to 20 amino acid residues;
FCS is a furin cleavage sequence of amino acid residues, which sequence is cleavable by furin and has an amino end and a carboxyl end;
$R^3$ is 1 to 20 amino acid residues;
$R^4$ is 1 or more contiguous residues of residues 365-394 of SEQ ID NO: 1; and

PE functional domain III is residues 395-613 of *Pseudomonas* exotoxin A (PE) SEQ ID NO: 1, wherein the molecule has a deletion of amino acid residues 253-273 and 285-364 as defined by SEQ ID NO: 1; and wherein the molecule optionally has (i) a substitution of one or more amino acid residues within one or more T-cell epitopes, (ii) a substitution of one or more amino acid residues within one or more B cell epitopes, (iii) a deletion of one or more contiguous amino acid residues of residues 1-252 as defined by SEQ ID NO:1; or (iv) a combination of any of (i)-(iii).

8. The molecule of claim 7, wherein the molecule has a substitution of one or more of amino acid residues R427, F443, R456, D463, R467, L477, R490, R494, R505, R538, and L552, as defined by reference to SEQ ID NO: 1, in PE functional domain III.

9. The molecule of claim 7 wherein the molecule has one or more of the following amino acid substitutions: R427A, F443A, R456A, D463A, R467A, L477H, R490A, R494A, R505A, R538A, and L552E, as defined by reference to SEQ ID NO: 1, in PE functional domain III.

10. The molecule of claim 7, wherein one or more of $R^1$, $R^2$, and $R^3$ consist(s) of 1 to 20 amino acid residues selected, independently, from the group consisting of lysine, alanine, glycine, and serine.

11. The molecule of claim 7, wherein one or more of $R^1$, $R^2$, and $R^3$ consist(s) of 1 to 20 amino acid residues selected, independently, from the group consisting of glycine and serine.

12. The molecule of claim 1, wherein the targeting moiety is a monoclonal antibody or an antigen binding portion thereof.

13. The molecule of claim 1, wherein the targeting moiety specifically binds to a cell surface marker selected from the group consisting of CD19, CD21, CD22, CD25, CD30, CD33, CD79b, BCMA, glypican 2 (GPC2), glypican 3 (GPC3), transferrin receptor, EGF receptor (EGFR), mutated EGFR, mesothelin, cadherin, and Lewis Y.

14. The molecule of claim 1, wherein the targeting moiety is an antibody selected from the group consisting of B3, RFB4, SS, SS1, MN, MB, HN1, HN2, HB21, MORAb-009, YP218, YP7, HN3, LH1, LH4, LH7, BM24, BM306, antigen binding portions of the foregoing, and an antigen binding portion of HA22.

15. A pharmaceutical composition comprising (a) the molecule of claim 1, and (b) a pharmaceutically acceptable carrier.

16. The molecule of claim 1, wherein the fourth domain contains only Domain III.

17. The molecule of claim 1, wherein the molecule comprises PE-LR.

18. The molecule of claim 1, wherein the fourth domain is PE24.

* * * * *